United States Patent
Liu et al.

(10) Patent No.: US 8,415,501 B2
(45) Date of Patent: Apr. 9, 2013

(54) METHODS AND COMPOSITIONS FOR MAKING AND USING POLYMORPHS OF CINACALCET

(75) Inventors: Belle B. Liu, Oak Park, CA (US); Pengzu Zhou, Thousand Oaks, CA (US); Nina Cauchon, Thousand Oak, CA (US)

(73) Assignee: Amgen, Inc., Thousand Oaks, CA (US)

( * ) Notice: Subject to any disclaimer, the term of this patent is extended or adjusted under 35 U.S.C. 154(b) by 1341 days.

(21) Appl. No.: 11/690,036

(22) Filed: Mar. 22, 2007

(65) Prior Publication Data

US 2007/0238790 A1    Oct. 11, 2007

Related U.S. Application Data

(60) Provisional application No. 60/785,294, filed on Mar. 23, 2006.

(51) Int. Cl.
*C07C 211/00* (2006.01)

(52) U.S. Cl. ............ 564/337; 564/336; 560/41; 560/28; 514/487; 514/649

(58) Field of Classification Search .................. None
See application file for complete search history.

(56) References Cited

U.S. PATENT DOCUMENTS

| | | | |
|---|---|---|---|
| 5,688,938 A | 11/1997 | Brown et al. | |
| 5,763,569 A | 6/1998 | Brown et al. | |
| 5,858,684 A | 1/1999 | Nemeth et al. | |
| 5,962,314 A | 10/1999 | Brown et al. | |
| 5,981,599 A | 11/1999 | Moe et al. | |
| 6,001,884 A | 12/1999 | Nemeth et al. | |
| 6,011,068 A | 1/2000 | Nemeth et al. | |
| 6,031,003 A | 2/2000 | Nemeth et al. | |
| 6,172,091 B1 | 1/2001 | Cohen et al. | |
| 6,211,244 B1 | 4/2001 | Van Wagenen et al. | |
| 6,313,146 B1 | 11/2001 | Van Wagenen et al. | |
| 6,342,532 B1 | 1/2002 | Moe et al. | |
| 6,362,231 B1 | 3/2002 | Sakai et al. | |
| 6,432,656 B1 | 8/2002 | Del Mar et al. | |
| 6,710,088 B2 | 3/2004 | Moe et al. | |
| 6,908,935 B2 | 6/2005 | Kelly et al. | |
| 7,176,322 B2 | 2/2007 | Kelly et al. | |
| 7,247,751 B2 | 7/2007 | Lifshitz-Liron et al. | |
| 7,250,533 B2 | 7/2007 | Lifshitz-Liron et al. | |
| 7,563,930 B2 * | 7/2009 | Wizel et al. | 564/337 |
| 2002/0107406 A1 | 8/2002 | Sakai et al. | |
| 2005/0101576 A1 | 5/2005 | Whitehouse et al. | |
| 2005/0147669 A1 * | 7/2005 | Lawrence et al. | 424/464 |
| 2006/0276534 A1 | 12/2006 | Martin et al. | |

FOREIGN PATENT DOCUMENTS

| | | |
|---|---|---|
| EP | 933354 | 8/1999 |
| WO | WO-93/04373 | 3/1993 |
| WO | WO-94/18959 | 9/1994 |
| WO | WO-95/11221 | 4/1995 |
| WO | WO-96/12697 | 5/1996 |
| WO | WO-97/41090 | 11/1997 |
| WO | WO-01/034562 | 5/2001 |
| WO | WO-2006/125026 | 11/2006 |
| WO | WO-2006/127932 | 11/2006 |
| WO | WO-2006/127933 | 11/2006 |
| WO | WO-2006/127941 | 11/2006 |
| WO | WO-2007/027548 | 3/2007 |
| WO | WO-2007/062147 | 5/2007 |
| WO | WO 2007/127445 | 11/2007 |
| WO | WO 2007/127449 | 11/2007 |

OTHER PUBLICATIONS

Berge et al., "Pharmaceutical salts," *J. Pharm. Sci.*, 66:1-19 (1977).
Braunwald et al., "Calcium, phosphorus, and bone metabolism: calcium-regulating hormones," (pp. 1860-1865), in Kasper et al., *Harrison's Principles of Internal Medicine*, New York: McGraw-Hill (1987).
Bruno et al., "New software for searching the Cambridge Structural Database and visualizing crystal structures," *Acta Cryst.*, B58:389-397 (2002).
Burla et al., "SIR2004: an improved tool for crystal structure determination and refinement," *J. App. Cryst.*, 38:381-388 (2005).
Chen et al., "Vascular calcification in chronic kidney disease," *Semin. Nephrol.*, 24:61-68 (2004).
Farrugia, "ORTEP-3 for Windows—a version of ORTEP-III with a graphical user interface," *J. Appl. Cryst.*, 30:565 (1997).
Flack et al., "Absolute structure and absolute configuration," *Acta Cryst.*, A55:908-915 (1999).
Flack et al., "Reporting and evaluating absolute-structure and absolute-configuration determinations," *J. Appl. Cryst.*, 33:1143-1148 (2000).
Flack, "On enantiomorph-polarity estimation," *Acta Cryst.* A39:876-881 (1983).
Holick, "Noncalcemic actions of 1,25-dihydroxyvitamin D3 and clinical applications," *Bone*, 17:107S-110S (1995).
International Search Report and Written Opinion, PCT/US2007/064700, dated Aug. 15, 2007.
Otwinowski et al., "Processing of x-ray diffraction data collected in oscillation mode," *Methods in Enzymology*, 276:307-326 (1997).
Proudfoot et al., "Biology of calcification in vascular cells: intima versus media," *Herz*, 26:245-251 (2001).
Stumpf et al., "Target cells for 1,25-dihydroxyvitamin D3 in intestinal tract, stomach, kidney, skin, pituitary, and parathyroid," *Science*, 206:1188-1190 (1979).
"N-[1-(R)-(−)-(1-napthyl)ethyl]-3-[3[3-(trifluoromethyl)phenyl]-1-aminopropane hydrochloride," IP.Com *Journal* (May 23, 2005).

* cited by examiner

*Primary Examiner* — Sudhakar Katakam
(74) *Attorney, Agent, or Firm* — Fitzpatrick, Cella, Harper & Scinto

(57) ABSTRACT

The present invention is directed to methods and compositions for making and using a new polymorph of cinacalcet hydrochloride.

23 Claims, 11 Drawing Sheets

METHODS AND COMPOSITIONS FOR MAKING AND USING POLYMORPHS OF CINACALCET

The present application claims the benefit of priority of U.S. Provisional Patent Application Ser. No. 60/785,294, which was filed Mar. 23, 2006. The entire text of the aforementioned application is incorporated herein by reference.

FIELD OF THE INVENTION

The present application is directed to crystalline polymorphs of the calcimimetic agent cinacalcet hydrochloride and methods and compositions of making and using the same.

BACKGROUND OF THE INVENTION

Sensipar® (cinacalcet) is a calcimimetic agent that has the chemical name N-[1-(R)-(−)-(1-naphthyl)ethyl]-3-[3-(trifluoromethyl)phenyl]-1-aminopropane hydrochloride, has the empirical formula $C_{22}H_{22}F_3N.HCl$ and the structural formula shown in FIG. 5. The molecular weight of the hydrochloride salt is 393.9 g/mol and the free base is 357.4 g/mol. There is one chiral center in the molecule, and the R enantiomer is the more potent enantiomer.

Cinacalcet hydrochloride is commercially available as Sensipar® or Mimpara®. The calcimimetic agent is used to increase the sensitivity of the calcium-sensing receptor to activation by extracellular calcium. This calcimimetic has been shown to be therapeutically effective in the treatment of patients with chronic kidney disease on dialysis that have secondary hyperparathyroidism and of hypercalcemia in patients with parathyroid carcinoma. Today there are more than 300,000 kidney dialysis patients with chronic kidney disease (CKD) in the U.S. alone. Nearly all of these patients suffer from secondary hyperparathyroidism (HPT), which is a progressive disease, associated with increases in parathyroid hormone (PTH) levels and abnormal calcium and phosphorus metabolism. In a typical patient having mild HPT, the iPTH levels are 300 to 500 pg/ml; a patient having moderate HPT has an iPTH of 500 to 800 pg/ml; and a patient with severe HPT has an iPTH of greater than 800 pg/ml. A normal iPTH level should be in the range of about 250 pg/ml. The lower limit of normal calcium level in humans is about 8.4 mg/dL. HPT can develop early during the course of CKD and continues to progress as kidney function declines. Untreated secondary HPT is characterized by abnormal calcium and phosphorus levels and is associated with serious consequences, including cardiovascular morbidity.

Increased PTH stimulates osteoclastic activity resulting in cortical bone resorption and marrow fibrosis. Sensipar® is the first treatment that meets a significant medical need in patients with secondary HPT to lower the levels of PTH, calcium, and phosphorus in the blood, in order to prevent progressive bone disease and the systemic consequences of disordered mineral metabolism. Reduction of PTH levels in CKD patients on dialysis with uncontrolled secondary HPT has been shown to have positive effects on bone-specific alkaline phosphatase (BALP), bone turnover and bone fibrosis.

PTH secretion is regulated through the action of a calcium-sensing receptor on the cell surface of the parathyroid gland. Sensipar® directly lowers PTH levels by increasing the sensitivity of this calcium-sensing receptor to extracellular calcium. The reduction in PTH is associated with a concomitant decrease in serum calcium levels.

Sensipar® is the only available therapy that allows practitioners to reduce PTH while lowering calcium-phosphorus product, which is consistent with the National Kidney Foundation's Kidney Disease Outcomes Quality Initiative (K/DOQI) clinical practice guidelines for bone metabolism and disease in chronic kidney disease. Prior to its development, the only available medical treatments for patients with secondary HPT were phosphate binders and vitamin D sterols, which may elevate calcium and/or phosphorus levels. Such elevation would frequently require treatment to be interrupted and lead to an inadequate control of PTH.

It is now well-accepted that Sensipar® provides an excellent targeted treatment of secondary HPT with its unique mechanism of action that acts directly on the calcium-sensing receptor. Sensipar® provides significant improvement over traditional therapy to provide an important new tool to help dialysis patients suffering from secondary HPT. It also is successful in lowering calcium levels in patients with hypercalcemia due to parathyroid carcinoma. Patients with parathyroid carcinoma have a rare, serious cancer of the parathyroid gland results in excess secretion of PTH. Thus, parathyroid carcinoma is one form of primary HPT. The disease is complicated by elevated calcium levels in the blood. High calcium levels can lead to anxiety, depression, nausea, vomiting, bone fractures, kidney stones and in some cases coma. Surgical removal of the parathyroid gland is the only curative therapy for this disease but is not successful in all cases. Sensipar® was shown to reduce high levels of calcium in patients with parathyroid carcinoma.

SUMMARY OF THE INVENTION

The present invention is directed to methods and compositions for making and using a polymorph of cinacalcet hydrochloride. In specific embodiments, the invention provides a crystalline polymorph of N-[1-(R)-(−)-(1-naphthyl)ethyl]-3-[3-(trifluoromethyl)phenyl]-1-aminopropane hydrochloride having a powder X ray powder diffraction (XRPD) pattern having peaks at diffraction angle 2 θ of about 16.6942; 17.6152; 19.4992; 20.2946; and 20.5877. In other embodiments, the XRPD pattern may further comprise at least one diffraction angle 2 θ peak selected from the group consisting of 12.3402; 14.4334; 15.3545; 16.443; 18.2013; 18.6618; 19.9178; 21.7599; 21.9692; 22.4297; 24.0206; and 25.0672.

In still other embodiments, the crystalline polymorph of the invention has an XRPD pattern comprises at least diffraction angle 2 θ peaks at about 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672.

In still other embodiments, the crystalline polymorph has an XRPD pattern comprises diffraction angle 2 θ peaks at about 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672.

In yet another embodiment, the crystalline polymorph comprises an XRPD pattern substantially as shown in FIG. 1, 2 or 3.

In additional embodiments, the crystalline polymorph may be defined according to FTIR spectra (e.g., positional parameters, anisotropic temperature factor coefficients, bond distance characteristics), bond angle characteristics, torsion angle characteristics, Raman spectra, NMR spectra or any combination of one or more of these characteristics of a polymorph. For example, the crystalline polymorph has positional parameters substantially as shown in Table 3 and/or an anisotropic temperature factor coefficient substantially as shown in Table 4, and/or bond distance characteristics substantially as shown in Table 5, and/or bond angle characteristics substantially as shown in Table 6, and/or torsion angle characteristics substantially as shown in Table 7. It should be noted that the polymorph may be defined by a combination of any or all of the foregoing parameters.

Another aspect of the invention contemplates a pharmaceutical composition comprising a polymorph as outlined above and at least one pharmaceutically acceptable carrier.

Also provided herein is a method of preparing a polymorph of cinacalcet, the method comprising melting cinacalcet polymorph Form I at 190° C. and quenching said amorphous form in a cooling bath of dry ice and acetone for 30 minutes; grinding said quenched amorphous form to produce an reduce particle size of said quenched amorphous form; and heating those amorphous quenched, size-reduced particles at 90° C. for approximately 3.5 hours. In specific embodiments, the size-reduced particles have a particle size of about 38 μm. In other embodiments, the size-reduced particles have a particle size of about 125 μm. Also contemplated is a polymorph of cinacalcet prepared according to this method. Optionally, such a polymorph is placed in a pharmaceutical composition with at least one pharmaceutically acceptable carrier. In certain specific aspects, the grinding of the quenched amorphous form to produce size-reduced particles produces a population of evenly distributed and/or evenly sized particles.

The invention also contemplates methods of treating a subject in need of a calcimimetic comprising administering a therapeutically effective amount of a polymorph of the present invention.

In specific embodiments, the subject is suffering from hyperparathyroidism and said therapeutically effective amount decreases the levels of parathyroid hormone (PTH) in said subject.

In other embodiments, the treatment method is for treating a subject that is suffering from chronic kidney disease associated with elevated PTH levels and said therapeutically effective amount of the polymorph decreases the symptoms of kidney disease in said subject. In certain other embodiments, the subject is suffering from secondary hyperparathyroidism associated with chronic kidney disease. In particular embodiments, the treatment method decreases the amount of kidney dialysis required by said subject is suffering from chronic kidney disease associated with elevated PTH levels and said therapeutically effective amount decreases the symptoms of kidney disease in said subject.

In still further embodiments, the therapeutically effective amount of the polymorph used in the method of treatment decreases the serum calcium levels of said subject as compared to the serum calcium levels of said subject in the absence of administration of said polymorph.

In still additional embodiments, the therapeutically effective amount of the polymorph used in the method decreases the serum phosphorus levels of said subject as compared to the serum phosphorus levels of said subject in the absence of administration of said polymorph.

Another aspect of the invention contemplates a method of preventing or decreasing progressive bone disease in a mammal comprising administering to said mammal a therapeutically effective amount of a polymorph as outlined above. In specific embodiments, the therapeutically effective amount of the polymorph is in the form of a pharmaceutical composition.

In the therapeutic methods of the invention, the polymorph may, for example be administered in an amount to achieve an iPTH less than or equal 250 pg/ml. In other embodiments, the polymorph is administered at a dose of about 20 mg per day to about 200 mg/day. In still additional embodiments, the dose of said polymorph is maintained at the dosage being administered if the subject has an iPTH less than or equal to 200 pg/ml. In still further embodiments, the dose of the polymorph is maintained at the dosage being administered if the subject has a serum calcium level of less than 7.8 mg/dL. The polymorph may be administered in combination with a composition comprising vitamin D or a vitamin D analog. In still other embodiments, the polymorph may be administered in combination with another calcimimetic agent. In still further embodiments, the polymorph may be administered in combination with a composition comprising an inhibitor of cytochrome P450 2D6. In yet further embodiments, the polymorph may be administered in combination with one or more agents selected from the group consisting of vitamin D or a vitamin D analog, a calcimimetic agent, and an inhibitor of cytochrome P450 2D6. In still further aspects of the invention, the polymorph may be administered in combination with one or more vitamin D analogs and/or one or more other calcimimetic agents, and/or one or more inhibitors of cytochrome P450 2D6.

Other aspects of the invention relate to treatment of a subject suffering from vascular calcification and said therapeutically effective amount decreases the formation, growth or deposition of extracellular matrix hydroxyapatite crystal deposits in the blood vessels of said subject. For example, such a subject may be suffering from coronary, valvular, aortic, or other blood vessel calcification. In still other embodiments, the subject is suffering from a kidney-related disorder, such as for example, polycystic kidney disease or a podocyte related disorder. Exemplary podocyte related disorders include podocytopenia, increased in the foot process width, effacement or a decrease in slit diaphragm length, a diminution of podocyte density or podocyte injury.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DETAILED DESCRIPTION OF THE CERTAIN EMBODIMENTS OF THE INVENTION

Figure 5:
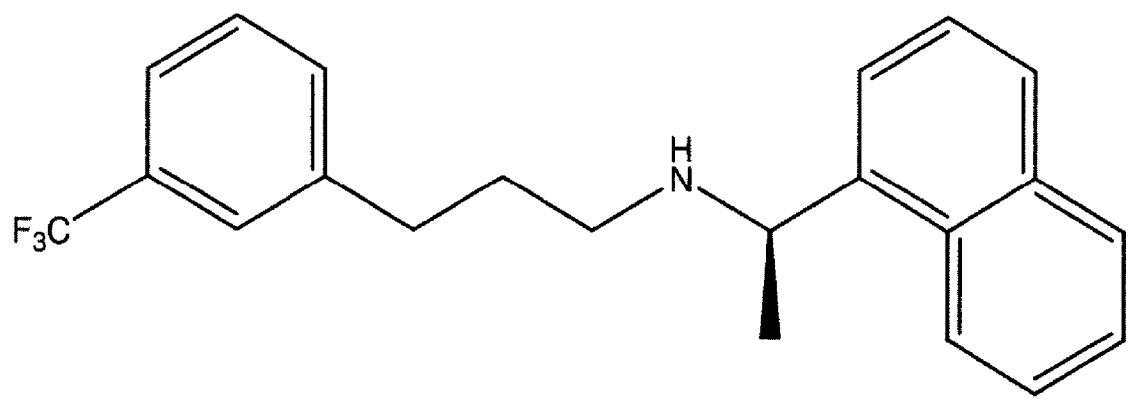
FIG. 5 shows the proposed molecular structure of cinacalcet Form III.

Cinacalcet HCl, the compound of formula shown in FIG. 5, has been commercially formulated as the agent Sensipar®. Previously, two separate solid forms of the compound have been described. The present invention describes an additional third form of the compound. These three distinct crystalline forms of cinacalcet HCl are referred to herein as Forms I, II, and III, and can be referred to as "polymorphs." Form II has been prepared but was unstable at room temperature. The present invention is directed to a novel polymorph Form III. Since the intended use of this compound is as a therapeutically active pharmaceutical agent, a stable and pharmaceutically acceptable form of this compound will be of great interest.

Polymorphism can be characterized as the ability of a compound to crystallize into different crystal forms, while maintaining the same chemical formula. A crystalline polymorph of a given drug substance is chemically identical to any other crystalline polymorph of that drug substance in containing the same atoms bonded to one another in the same way, but differs in its crystal forms, which can affect one or more physical properties, such as stability, solubility, melting point, bulk density, flow properties, bioavailability, etc. Thus, the term "polymorph" is used to refer to a crystalline form of a substance that is distinct from another crystalline form but that shares the same chemical formula.

"Effective" or "therapeutically effective" is meant to describe a polymorph of a compound or a composition of the present invention effective as a calcimimetic and thus producing the desired therapeutic, ameliorative, inhibitory or preventative effect of Sensipar®. While the level or degree of calcimimetic, therapeutic, ameliorative, inhibitory or preventative effect in some embodiments is the same or better than that seen when Sensipar® is used, the level or degree of such an effect may be less than that observed with Sensipar® as long as it is more than, or better than the effect seen in the absence of any calcimimetic. The "effect" may be a biochemical physiologic effect such as a lowering of serum calcium levels in a hypercalcemic patient, lowering of PTH levels, or lowering of serum phosphorus levels. Alternatively, the "effect" may be one that is observed as a result of achieving a therapeutic lowering of serum calcium levels, PTH levels and the like, such as for example, an amelioration of the symptoms of CKD, a decrease in symptoms associated with increased calcium levels (e.g., lowering of anxiety, depression, nausea, vomiting, bone fractures, kidney stones, vascular or soft-tissue calcification, and in some cases decreased likelihood of coma).

While the present invention particularly contemplates an isolated composition of a purified cinacalcet hydrochloride polymorph III, it is contemplated that the skilled person may prepare compositions in which the isolated, purified polymorph III is mixed with, for example, polymorph I or II.

In addition, in compositions for use in the present invention, it should be understood that the skilled person may prepare pharmaceutical or other therapeutic compositions which comprise the polymorph III described herein in combination with another agent that is used as a calcimimetic. Such combination therapy compositions may be used to have a combined effect as a calcimimetic combination therapy to produce a desired therapeutic, ameliorative, inhibitory or preventative PTH-lowering or calcium-lowering effect.

In the therapeutic embodiments of the invention, the compositions can be administered and the effects of the compositions are routinely monitored to avoid the subject becoming hypocalcemic, therefore lowering the serum calcium levels to less than 7.8 mg/dL should be avoided. In other embodiments, the calcimimetic therapy is administered in order to lower the PTH levels in the subject, the PTH levels are lowered to levels of about 250 pg/ml. However, the therapies should be monitored and adjusted to avoid lowering the PTH levels to less than 150 pg/ml. Thus, the therapies should be designed in order to lower and maintain the PTH levels to a range of between about 200 pg/ml to about 300 pg/ml.

Thus, in a typical treatment regimen, it is contemplated that a daily dose of the polymorph III is administered to achieve PTH levels in the subject of from about 150 pg/ml to about 300 pg/ml. Thus, in certain embodiments, the subject is initiated on a therapeutic regimen in which a dosage form of about 5 mg, 10 mg, 15 mg, 20 mg, 25 mg, or 30 mg is administered daily. The PTH levels in the subject are monitored prior to and after administration of the composition. The dosage of the polymorph can be increased to a level where the dosage has the desired therapeutic effect of maintaining the level of PTH to a level of from 200 pg/ml to about 300 pg/ml. Where it is seen that the PTH levels in the subject are higher than 300 pg/ml, the dosage of the polymorph administered may be increased. If the level of the PTH is seen to be at or about 200 pg/ml, the dosage of the polymorph should be maintained or lowered. If the level of the PTH is seen to be below 200 pg/ml, the dosage of the polymorph should be lowered. The PTH concentration can be monitored and the polymorph administration regimen reinitiated when and if the patient's PTH levels again reach 300 pg/ml or greater. Likewise, the serum calcium levels can be monitored in response to the treatment with the polymorph III such that the serum calcium levels are maintained at or above the lower limit of the normal level of serum calcium, which is about 8.4 mg/dL. If the blood work shows that the treatment with the polymorph is resulting in the decrease of serum calcium levels to the range of between 7.8 mg/dL to about 8.4 mg/dL the dosage of the polymorph should be decreased and/or combined with calcium-containing phosphate binders and/or vitamin D sterols. If the calcium levels fall below 7.5 mg/dL the calcimimetic therapy should be stopped and/or the amount of vitamin D sterols and/or calcium-containing phosphate binders should be increased until the serum calcium levels are again above 8.4 mg/dL.

Cinacalcet Hydrochloride Polymorph III and Methods of Preparing and Characterizing the Same This disclosure provides novel polymorph of cinacalcet hydrochloride. The disclosure further provides pharmaceutical compositions and formulations using such polymorph. The pharmaceutical compositions and formulations are adapted for various forms of administration including oral, injection and/or inhalation. The disclosure also provides methods for making the novel cinacalcet hydrochloride polymorph, methods of manufacturing pharmaceutical formulations of cinacalcet hydrochloride polymorph and methods of treating various diseases such as, for example, HPT, parathyroid carcinoma, and other hypercalcemia-related disorders.

In one aspect, the polymorph Form III of the invention is able to modulate calcium receptor activity and is used in the treatment of diseases or disorders which can be affected by modulating one or more activities of a calcium receptor. As noted above, $Ca^{2+}$ levels are tightly controlled is and it $Ca^{2+}$ levels in turn control various processes such as blood clotting, nerve and muscle excitability, and proper bone formation. For example, extracellular $Ca^{2+}$ inhibits the secretion of parathyroid hormone from parathyroid cells, inhibits bone resorption by osteoclasts, and stimulates secretion of calcitonin from C-cells. In one aspect, the disease or disorder to be treated by cinacalcet can be characterized by abnormal bone and mineral homeostasis, such as calcium homeostasis. Abnormal calcium homeostasis is characterized by one or more of the following activities: (1) an abnormal increase or decrease in serum calcium; (2) an abnormal increase or decrease in urinary excretion of calcium; (3) an abnormal increase or decrease in bone calcium levels, for example, as assessed by bone mineral density measurements; (4) an abnormal absorption of dietary calcium; (5) an abnormal increase or decrease in the production and/or release of messengers which affect serum calcium levels such as parathyroid hormone and calcitonin; and (6) an abnormal change in the response elicited by messengers which affect serum calcium levels. The abnormal increase or decrease in these different aspects of calcium homeostasis is relative to that occurring in the general population and is generally associated with a disease or disorder.

Specific diseases and disorders which might be treated or prevented, based upon the affected cells, also include those of the central nervous system such as seizures, stroke, head trauma, spinal cord injury, hypoxia-induced nerve cell damage such as in cardiac arrest or neonatal distress, epilepsy, neurodegenerative diseases such as Alzheimer's disease, Huntington's disease and Parkinson's disease, dementia, muscle tension, depression, anxiety, panic disorder, obsessive-compulsive disorder, post-traumatic stress disorder, schizophrenia, neuroleptic malignant syndrome, and Tourette's syndrome; diseases involving excess water reabsorption by the kidney such as syndrome of inappropriate ADH secretion (SIADH), cirrhosis, congestive heart failure, and nephrosis; hypertension; preventing and/or decreasing renal toxicity from cationic antibiotics (e.g., aminoglycoside antibiotics); and autoimmune diseases and organ transplant rejection. In addition, bone and mineral-related disorders (as described in Coe and Favus, Disorders of Bone and Mineral Metabolism, Raven Press, 1990), kidney diseases, endocrine diseases, cancer, cardiovascular diseases, neurological diseases, and diseases associated with gestation also can be treated.

In certain embodiments, the compositions will be useful in treating or ameliorating psoriasis by reducing the proliferation of the abnormal skin cells. In other embodiments, the compositions may be used to reduce water retention in states of vasopressin excess, such as the syndrome of inappropriate vasopressin (ADH) secretion. The polymorph III may be useful for treating hypertension by: (a) reducing renin secretion and/or (b) by stimulating production of vasodilators such as PTHrP (PTH-related peptide) by vascular smooth muscle. It also is contemplated that the polymorph Form III may be used to increase platelet aggregability, which may be useful when platelet counts are low. Calcium also is known to promote differentiation of colon and mammary cells, as such the polymorph Form III may be expected to reduce the risk of colon or breast cancer. As a calcimimetic, cinacalcet Form III is expected to have a useful hypocalcemic action in the therapy of hypercalcemic disorders. The inhibitory effect of calcimimetics on osteoclasts and their stimulation of the secretion of the hypocalcemic peptide calcitonin make them useful in the therapy of hypercalcemia and its symptoms. The cinacalcet Form III also improves hypocalcemic symptoms by activating calcium receptors. In addition, calcium suppresses the formation of 1,25-dihydroxyvitamin D in the proximal renal tubule, and this vitamin D metabolite is frequently overproduced in renal stone patients and contributes to their hypercalciuria. Suppression of 1,25-dihydroxyvitamin D formation by a calcimimetic such as cinacalcet Form III is expected to be useful in treating renal calcium stone disease.

The therapeutic cinacalcet Form III preparations will likely be used in the treatment of human subjects but it should be understood that veterinary treatments also are contemplated and the compositions may be used to treat other primates, farm animals such as swine, cattle, and poultry; and sports animals and pets such as horses, dogs and cats.

For additional methods and compositions for using cinacalcet-related compositions and diseases to be treated by such compositions, those of skill are referred to U.S. Pat. Nos. 6,011,068; 6,031,003; 6,211,244; 6,313,146, each incorporated herein by reference in its entirety.

As used herein, the term "amorphous" refers to samples lacking a well-defined peak or having a broad "halo" feature in the X-ray powder diffraction (XRPD) pattern of the sample. The term "amorphous" may also refer to a material that contains too little crystal content to yield a discernable pattern by XRPD or other diffraction techniques. Glassy materials are contemplated to be amorphous. Amorphous materials do not have a true crystal lattice, and are consequently glassy rather than true solids, technically resembling very viscous non-crystalline liquids. Rather than true solids, glasses may better be described as quasi-solid amorphous material. Thus, an amorphous material may refer to a quasi-solid glassy material. Precipitation of a compound from solution, often effected by rapid evaporation of solvent, is known to favor amorphous forms of a compound.

As used herein, the term "broad" or "broadened" is used to describe spectral lines including XRPD, nuclear magnetic resonance (NMR) spectroscopy and infrared (IR) spectroscopy lines is a relative term that relates to the line width of a baseline spectrum. The baseline spectrum is often that of an unmanipulated crystalline (defined below) form of a specific compound as obtained directly from a given set of physical and chemical conditions, including solvent composition and properties such as temperature and pressure, for example describing the XRPD spectrum of ground or pulverized crystalline material relative to the crystalline material prior to grinding. Line broadening is indicative of increased randomness in the orientation of the chemical moieties of the compound, thus indicative of an increased amorphous content. When comparisons are made between crystalline materials obtained via different crystallization conditions, broadening indicates either increased amorphous content of the sample having the broadened spectral lines, or possibly a mixture of crystals that have similar, although not identical spectra.

The specific crystal form of the agent will dictate the thermodynamic stability of the crystal. Depending on the form of the specific type of crystal present, various amounts of amorphous solid material containing the specific compound will be present. Such amorphous solid material may be present as a side product of the initial crystallization, and/or a product of degradation of the crystals comprising the crystalline material. Thus, "crystalline" as used herein contemplates amorphous content of varying degrees so long as the material has a discernable diffraction pattern. Often the amorphous content of a crystalline material may be increased by grinding or pulverizing the material, which is evidenced by broadening of diffraction and other spectral lines relative to the unground crystalline material. Sufficient grinding and/or pulverizing may broaden the lines relative to the unground crystalline material to the extent that the XRPD or other crystal specific spectrum may become undiscernable, making the material substantially amorphous, or barely discernable, which may be termed quasi-amorphous.

As used herein, the term "trace" refers to an amount that is detectable by the physical and chemical detection methods employed herein. For example, water, crystallization solvents, amorphous forms of cinacalcet may all be present in trace amounts of Form III while not significantly affecting the XRPD, NMR, or IR spectral measurements of the sample nor its biological activity.

In some instances, the polymorph may be a crystalline anhydrate, monohydrate, and hemihydrate. Amorphous polymorphs can be derived by rapidly evaporating solvent from solvated cinacalcet, or by grinding, pulverizing or otherwise physically pressurizing or abrading any of the various crystalline amorphous forms described herein. General methods for precipitating and crystallizing organic compounds may be applied to preparing any cinacalcet polymorphs. These general methods are known to those skilled in the art of synthetic organic chemistry and pharmaceutical formulation, and are described, for example, by J. March, "Advanced Organic Chemistry: Reactions, Mechanisms and Structure," 4th Ed. (New York: Wiley-Interscience, 1992).

In specific embodiments, the Form III was prepared using "cold finger sublimation." Sublimation is the term used for transformation of a compound directly from the solid to the gaseous state or from the gaseous to the solid state without becoming a liquid. The apparatus for performing this process typically has a section where the compound to be sublimed is placed and a cooler section above this section where the purified material will collect. Typically, the compound is heated and collected on a chilled piece called a cold finger, thus, the "cold finger" is a common name for a chilled tubing used in the sublimation experiment. In the preparation of cinacalcet form III, the solid Form I is heated to gaseous state in a flask under vacuum and the crystal Form III accumulates on the surface of the cold finger that is inserted in the flask. Usually cooling water or dry ice are used to cool the cold finger. Polymorph III may be obtained in the following manner. Sublimation of Form I leads to formation of Form III. Sublimation was carried out on the Form I material on a laboratory scale using a cold finger sublimation apparatus. The apparatus was immersed in a silicone oil bath and the cold finger was water-cooled. The system was sealed under vacuum. Vacuum was not released until the final solids were harvested. The solids were observed through optical microscopy and characterized by XRPD analysis.

In certain other embodiments, the Form III is prepared from melt-quenched amorphous material. In this process, Form I is melted at approximately 190-200° C. It is then quenched in cold bath (dry ice+acetone) for at least 15 minutes. The material is then ground into a fine powder, which is then heated at 90° C. for approximately 3.5 hours to produce the Form III.

The present invention identified Form III of cinacalcet as a metastable form. While a variety of solvent systems and crystallization methods were utilized, a short-range ordered material was observed by XRPD analysis. The XRPD patterns observed in the capillary screen were all similar to the pattern observed for the initial Form III crystal. Additional thermal treatment of selected capillaries did not appear to produce a different material as determined by optical microscopy and subsequent XRPD analysis.

Crystals of cinacalcet Form III suitable for structure determination were obtained from a coldfinger sublimation of Form I solids. The crystal structure of Form III contains two cinacalcet HCl molecules in the asymmetric unit. The difference between the two molecules is the aromatic ring containing the trifluoromethyl group is rotated approximately 180°. The Form III molecules have a layered packing motif and are connected through one-dimensional hydrogen bonding interactions.

Preparation of amorphous samples was attempted through a number of techniques: namely, melt/quench, spray drying and also cryogenic grinding of Form I solids. All three techniques yielded the amorphous material, which could then be used to prepare the Form III. The cryogrind, melt/quench, and spray dried materials were analyzed by X-ray powder diffraction (XRPD), but also could be analyzed by variable-temperature XRPD, to determine a relationship between the crystalline and short-range ordered materials. Pure Form III was readily prepared from amorphous material that is made using melt/quench and the spray dried techniques. The cryogenic grinding technique tends to yield mixtures of the Form I and Form III.

As noted above, one method of preparing Form III is to use melt-quenched amorphous material. To prepare melt/quenched amorphous material, Form I is melted at 190-200° C. It is then quenched in an ice bath (dry ice+acetone) for at least 15 minutes. The process produces the amorphous material which can then be used to prepare Form III.

In the cryogenic grinding procedure, Form I is freeze-milled under liquid nitrogen for approximately 40 minutes. This produces amorphous material that can then be used to prepare Form III. The Form III is prepared by heating the amorphous form at 90° C. for 3.5 hours. This procedure tends to yield a mixture of Form I and Form III.

In another exemplary procedure for preparing amorphous material, spray-drying can be used. In an exemplary spray drying technique 10 mg/mL Form I solution in toluene solvent was spray dried and collected under the conditions shown in the following Table:

| | |
|---|---|
| $N_2$ drying flow rate: | 350 SLPM-550 SLPM |
| Atom Pressure ($N_2$): | 30-50 psi |
| Inlet T: | 165° C. |
| Outlet T: | ~108° C. |
| Flow rate: | 0.5-1.0 mg/min |
| Nozzle T (bath): | 20° C. |
| Cyclone T (bath): | 20° C. |

Again, the amorphous material that results from the spray drying technique is then used to prepare Form III as discussed above, i.e., heating at 90° C. for 3.5 hours.

X-ray powder diffraction (XRPD) analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40°2θ was used. A silicon standard was analyzed to check the instrument alignment. Data were collected and analyzed using XRD-6000 v.4.1. Samples were prepared for analysis by placing them in an aluminum holder with silicon insert.

X-ray powder diffraction (XRPD) analyses also were performed using an Inel XRG-3000 diffractometer equipped with a CPS (Curved Position Sensitive) detector with a 2θ range of 120°. Real time data were collected using Cu—Kα radiation starting at approximately 4°2θ at a resolution of 0.03°2θ. The tube voltage and amperage were set to 40 kV and 30 mA, respectively. The monochromator slit was set at 5 mm (or 2 mm) by 160 µm. The pattern is displayed from 2.5-40°2θ. Samples were prepared for analysis by packing them into glass capillaries 1.0 mm in diameter. Each capillary was mounted onto a goniometer head that is motorized to permit spinning of the capillary during data acquisition. The samples were analyzed for 5 min. Instrument calibration was performed using a silicon reference standard.

X-ray powder diffraction (XRPD) analyses also were performed on prepared capillaries using a Bruker D-8 Discover diffractometer and Bruker's General Area Diffraction Detection System (GADDS, v.4.1.14). An incident beam of Cu Kα radiation was produced using a fine-focus tube (40 kV, 40 mA), a Göbel mirror, and a 0.5 mm double-pinhole collimator. Capillaries were positioned on a capillary holder secured to a translation stage. A video camera and laser were used to position the area of interest to intersect the incident beam. Samples were analyzed in transmission mode using a constant detector angle (2θ) of 20°. The incident beam was scanned 10° relative to the capillary surface normal and rastered ±1.0 mm along the length of the capillary during the analysis. Scanning and rastering the incident beam optimizes orientation statistics and maximizes the diffraction signal. Diffraction patterns were collected in 100 seconds using a Hi-Star area detector located 14.94 cm from the sample and processed using GADDS. The intensity in the GADDS image of the diffraction pattern was integrated from approximately 2° to 37° 2θ and from −163° to −17° chi using a step size of 0.04° 2θ. The integrated patterns display diffraction intensity as a function of 2θ.

Variable-temperature XRPD (VT-XRPD) was performed on a Shimadzu XRD-6000 X-ray powder diffractometer equipped with an Anton Paar HTK 1200 high temperature stage. The sample was packed in a ceramic holder and analyzed from 2.5 to 40°2θ at 3°/min (0.4 sec/0.02° step). Ramp rates and hold times for each experiment may be varied and such variations are known to those of skill in the art of operating X-ray powder diffractometer equipment. A silicon standard was analyzed to check the instrument alignment. Temperature calibration was performed using vanillin and sulfapyridine standards. Data were collected and analyzed using XRD-6000 v.4.1. VT-XRPD was performed on as-received short-range ordered material as well as materials prepared through quenching of a melt and cryogenic grinding.

Differential scanning calorimetry (DSC) also can be performed for the crystalline materials using a TA Instruments differential scanning calorimeter 2920, or other similar instrument. The sample was placed into an aluminum DSC pan, and the weight accurately recorded. The pan was covered with a lid and then crimped. In such an analysis, the sample cell is equilibrated at 25° C. and heated under a nitrogen purge at a rate of 10° C./min. The crystalline material is typically heated to 350° C., and transition maxima temperatures are noted.

Thermogravimetric (TG) analysis can be performed for crystalline material using a TA Instruments 2950 thermogravimetric analyzer or other similar instrument. The sample is placed in an aluminum sample pan and inserted into the TG furnace. The furnace is first equilibrated at 25° C., then heated under nitrogen at a rate of 10° C./min, up to a final temperature of 350° C. Nickel and Alumel™ can be used as the calibration standards.

FT-Raman spectrum also can be acquired for the polymorph III on an FT-Raman 960 spectrometer (Thermo Nicolet) or other similar instrument. This spectrometer uses an excitation wavelength of 1064 nm. Approximately 0.7 W of Nd:YVO$_4$ laser power is used to irradiate the sample. The Raman spectrum is measured with an indium gallium arsenide (InGaAs) detector. The sample is prepared for analysis by placing the material in a glass tube and positioning the tube in a gold-coated tube holder in the accessory. Sample scans (e.g., typically in the order of approximately 250 sample scans) are collected from 3600-98 cm$^{-1}$ at a spectral resolution of 4 cm$^{-1}$, using Happ-Genzel apodization. Wavelength calibration was performed using sulfur and cyclohexane.

For NMR analysis, a solution $^1$H nuclear magnetic resonance (NMR) spectrum can be acquired at ambient temperature using e.g., a Varian UNITY INOVA-400 or other similar spectrometer at a $^1$H Larmor frequency of 399.804 MHz. The sample is dissolved in DMSO-d$_6$. The spectrum is acquired with a $^1$H pulse width of 7.8 Vs, a 2.50 second acquisition time, a 5 second delay between scans, a spectral width of 6400 Hz with 32000 data points, and 40 co-added scans. The free induction decay (FID) is processed using the Varian VNMR 6.1C software with 65536 points and an exponential line broadening factor of 0.2 Hz to improve the signal-to-noise ratio. The residual peak from incompletely deuterated DMSO is typically seen at approximately 2.50 ppm. The spectrum can be referenced with an internal reference, e.g., to internal tetramethylsilane (TMS) at 0.0 ppm.

The crystalline material also may be characterized using optical microscopy e.g., performed with a Leica DM LP polarizing microscope (or other similar instrument), with a 5.0× objective, crossed-polarizers and a first order red compensator and Leica stereoscopes, with 0.8× to 10× objectives, with and without crossed-polarizers and a first order red compensator. Samples can be viewed in vials or glass microbeakers, or on coverglasses or glass slides (often with a drop of Paratone-N).

Pharmaceutical Compositions and Combination Therapy

The present invention describes a new polymorph, polymorph Form III, of cinacalcet hydrochloride. Those of skill in the art will be able to prepare pharmaceutical compositions from the polymorph(s) described by this invention. Such compositions typically will be formulated with inert, pharmaceutically acceptable carriers, and can be either formulated as solid or liquid forms. Solid form preparations include powders, tablets, dispersible granules, capsules, cachets and suppositories. The powders and tablets may be comprised of from about 5 to about 95 percent active ingredient. Suitable solid carriers are known in the art, e.g., lactose, sucrose, glucose, starch powder, crystalline cellulose, cellulose esters of alkanoic acids, polyvinyl alcohol, methyl cellulose, gum arabic, gelatin, gelatin, sodium alginate, hydroxypropyl cellulose, polyvinyl-pyrrolidine, polyethylene glycol, hydrogenated vegetable oil, magnesium stearate, magnesium oxide, stearic acid, sodium and calcium salts of phosphoric and sulphuric acids, and talc. Tablets, powders, cachets and capsules can be used as solid dosage forms suitable for oral administration. Examples of pharmaceutically acceptable carriers and methods of manufacture for various compositions may be found in R. C. Rowe (ed) Handbook of Pharmaceutical Excipients 4$^{th}$ Edn., 2003 Pharmaceutical Press London, and A. Gennaro (ed.), Remington's Pharmaceutical Sciences, 18th Edition, (1990), Mack Publishing Co., Easton, Pa. Alternatively, the compounds useful in this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The new polymorph, Form III will preferably be formulated and used in the form of pharmaceutically acceptable salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, mandelate, methanesulfonate, nicotinate, 2-naphthalenesulfonate, oxalate, palmoate, pectinate, persulfate, 2-phenylpropionate, picrate, pivalate, propionate, salicylate, succinate, sulfate, tartrate, thiocyanate, tosylate, mesylate, and undecanoate. When compounds of the invention include an acidic function such as a carboxy group, then suitable pharmaceutically acceptable salts for the carboxy group are well known to those skilled in the art and include, for example, alkaline, alkaline earth, ammonium, quaternary ammonium cations and the like. For additional examples of "pharmacologically acceptable salts," see Berge et al. J. Pharm. Sci. 66: 1, 1977. In certain embodiments of the invention salts of hydrochloride and salts of methanesulfonic acid can be used.

In some embodiments, the solid pharmaceutical compositions may be formulated in a manner similar to the formulation of Sensipar® tablets (see Physician's Desk Reference, 2006). Exemplary such compositions, in addition to containing the active ingredient of the polymorph III, also may contain inactive ingredients such as pre-gelatinized starch, microcrystalline cellulose, povidone, crospovidone, colloidal silicon dioxide, and magnesium stearate. Tablets are coated with color (Opadry® II green) and clear film-coat (Opadry® clear), carnauba wax, and Opacode® black ink. These coating compositions are simply exemplary coating compositions known to be used in Sensipar®, the skilled person will be well aware of number other coatings that could be used with the compositions of the invention.

In one embodiment, the cinacalcet Form III of the invention is prepared into a capsule formulation which comprises 22.0% cinacalcet Form III, 10.0% Starch 1500; 67.5% microcrystalline cellulose (e.g., microcrystalline cellulose PH101) and 0.5% talc. An exemplary such capsule comprises in per capsule 33.05 mg cinacalcet Form III; 15.00 mg Starch 1500, 101.19 mg microcrystalline cellulose (e.g., microcrystalline cellulose PH101) and 0.75 mg talc. Of course this is merely an exemplary capsule formulation and it should be understood that the weight of the cinacalcet Form III in such a capsule may vary from about 15% to about 30% of the capsule weight with the weights of the other ingredients being adjusted accordingly. Further it should be understood that Starch 1500, microcrystalline cellulose (e.g., microcrystalline cellulose PH1101) and talc may all be substituted with other pharmaceutically acceptable components.

In addition to solid forms, liquid forms, e.g., solutions, suspensions and emulsions, of the composition also may be prepared. For example, water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The polymorph may be deliverable through any route routinely used for the administration of a medicament so long as the target tissue is available via that route. Typical routes of administration include administration by orthotopic, intradermal subcutaneous, intramuscular, intraperitoneal, intrathecal, or intravenous injection. Alternatively, oral, nasal, buccal, rectal, vaginal or topical administration also are contemplated. One or more of the compositions used herein may be administered through intravenous injection. Such injections compositions would normally be administered as pharmaceutically acceptable compositions that include physiologically acceptable carriers, buffers or other excipients. For treatment of carcinoma, direct intratumoral injection, injection of a resected tumor bed, regional or general administration is contemplated. It also may be desired to perform continuous perfusion over hours or days via a catheter to a disease site, e.g., at the site of the parathyroid gland.

In specific embodiments, the medicament may be administered transdermally. The transdermal composition can take the form of creams, lotions, aerosols and/or emulsions and can be included in a transdermal patch of the matrix or reservoir type as are conventional in the art for this purpose.

In some embodiments, the polymorph is administered orally.

In certain exemplary embodiment, the pharmaceutical preparation is prepared in a unit dosage form. In such form, the preparation is subdivided into suitably sized unit doses containing appropriate quantities of the active component, e.g., an effective amount to achieve the desired purpose. Guidance for dosage forms may be obtained from the unit doses of Sensipar® that are routinely available. For example, the unit dose may be one which contains 10 mg, 20 mg, 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg in a single dosage form. Single unit dosage forms will contain either 30 mg, 60 mg, or 90 mg per unit dose.

The quantity of active compound in a unit dose of preparation may be varied or adjusted from about 0.01 mg to about 1000 mg, for example, from about 0.01 mg to about 750 mg, from about 0.01 mg to about 500 mg, and from about 0.01 mg to about 250 mg, according to the particular application.

The actual dosage employed in the treatment of a given subject may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition, and size of the patient as well as severity of the symptoms being treated. A typical recommended daily dosage regimen for oral administration can range from about 0.4 mg/day to about 1000 mg/day, in one to four daily doses.

In certain aspects of the present invention, it is contemplated that the polymorph compositions of the present invention may be administered in combination with one or more other therapeutic agent that is useful in the treatment of the disorder being treated by the calcimimetic.

For treatment of HPT, the polymorph may be administered in combination with vitamin D, vitamin D-related analogs and steroids, calcium blockers, and the like. Vitamin D is a generic term for a family of secosteroids that have affinity for the vitamin D receptor, and are involved in the physiologic regulation of calcium and phosphate metabolism. See Harrison's Principles of Internal Medicine: Part Eleven, "Disorders of Bone and Mineral Metabolism," E. Braunwald et al., (eds.), 1987, McGraw-Hill, New York at Chapter 335, pp. 1860-1865, Stumpf et al., 1979, Science 206:1188-90, and Holick, 1995, Bone 17:107 S-11S. Vitamin D exhibits a complex set of actions and mechanisms of synthesis. Cholecalciferol (vitamin D3) is synthesized in the skin following ultraviolet radiation from 7-dehydrocholesterol. Vitamin D2, an analog of vitamin D3, can be ingested from the diet. Two sequential hydroxylations of vitamin D2 are necessary for full biological activity. The first hydroxylation, which takes place in the liver, results in the formation of 25-hydroxycholecalciferol, while the second hydroxylation takes place in the kidney and results in the formation of the most potent biological metabolite of vitamin D: 1α,25-dihydroxycholecalciferol (also known as calcitriol).

Typically, the active vitamin D compound may be administered, for example, once a week at a dose of at least 0.12 µg/kg per day (8.4 µg in a 70 kg person). Pharmaceutical compositions may be administered in the form for oral, intravenous, intramuscular, topical, transdermal, sublingual, intranasal, intratumoral, or other preparations. Such compositions may comprise 5-100 µg of active vitamin D compound. For further descriptions of compositions comprising vitamin D steroids those of skill in the art are referred to U.S. Patent Application No. 20050101576.

The polymorphs may be administered in combination with other calcimimetic agents, such as e.g., the calcimimetic agents disclosed in U.S. Pat. Nos. 5,688,938, 5,763,569, 5,858,684, 5,962,314, 6,001,884, 6,011,068, 6,031,003, 6,211,244, 6,313,146, 6,908,935; and 7,176,322, AU 1,400, 801 and WO 01/34562. In those embodiments in which the polymorph is used for the treatment of hypercalcemia in patients with parathyroid carcinoma, the polymorph may be administered in combination with any antineoplastic intervention that is used for the treatment of carcinoma. Antineoplastic intervention includes but is not limited to radiotherapy, chemotherapy and even surgical resection of the parathyroid gland. Traditional antineoplastic agents include gemcitabine, paclitaxel (Taxol®), 5-Fluorourcil (5-FU), cyclophosphamide (Cytoxan®), temozolomide, or Vincristine. Antineoplastic agents typically fall into a number of subclasses of agents, namely, alkylating agents, antimetabolites, natural products and their derivatives, hormones and steroids (including synthetic analogs), and synthetics. Examples of compounds within these classes are given below.

Exemplary alkylating agents (including nitrogen mustards, ethylenimine derivatives, alkyl sulfonates, nitrosoureas and triazenes) for use in combination with the polymorph III of the invention include Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide. Antimetabolites, e.g., folic acid antagonists, pyrimidine analogs, purine analogs and adenosine deaminase inhibitors, that may be useful include Methotrexate, 5-Fluorouracil, Floxuridine, Cytarabine, 6-Mercaptopurine, 6-Thioguanine, Fludarabine phosphate, Pentostatine, and Gemcitabine. Other chemotherapeutic agents that may be used include the vinca alkaloids, antitumor antibiotics, enzymes, lymphokines and epipodophyllotoxins that are exemplified by compounds such as Vinblastine, Vincristine, Vindesine, Bleomycin, Dactinomycin, Daunorubicin, Doxorubicin, Epirubicin, Idarubicin, paclitaxel (paclitaxel is commercially available as Taxol®), Mithramycin, Deoxycoformycin, Mitomycin-C, L-Asparaginase, Interferons (especially IFN-α), Etoposide, and Teniposide.

The combination therapy also may be with hormones and steroids such as 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex. Other agents that could be used include Cisplatin, Carboplatin, Hydroxyurea, Amsacrine, Procarbazine, Mitotane, Mitoxantrone, Levamisole, and Hexamethylmelamine.

Methods for administering chemotherapeutic agents are known to those skilled in the art. In addition, their administration is described in the standard literature. For example, the administration of many of the chemotherapeutic agents is described in the "Physicians' Desk Reference" (PDR), e.g., 2006 edition (Medical Economics Company, Montvale, N.J. 07645-1742, USA); the disclosure of which is incorporated herein by reference thereto.

In addition to treatment with an additional therapeutic agent may be one which increases the effectiveness of the polymorph. For example, it is known that Sensipar® is metabolized by cytochrome P450 2D6. Co-administration of the polymorph with an agent that inhibits the activity of cytochrome P450 2D6 may be useful in increasing the efficacy of the polymorph Exemplary inhibitory agents include e.g., ketoconazole, erythromycin, itraconazole, fluconazole and the like. Co-administration of the polymorph with a cytochrome P450 2D6 inhibitor will allow a lower dosage of the polymorph to be therapeutically effective as compared to a dosage of the polymorph or even Sensipar® that is administered in the absence of an inhibitor of cytochrome P450 2D6. During such coadministration, serum calcium levels can be monitored to optimize the dosage of the polymorph.

In addition to HPT, carcinoma or other hypercalcemia-related disorders discussed above, it is contemplated that the compositions of the invention also may be used in the treatment of a variety of other disorders. As noted above, kidney related disorders may be particularly well-suited for therapeutic intervention with the cinacalcet Form III compositions of the invention. In certain embodiments, the compositions of the invention may be useful in the treatment or prevention of podocyte dysfunction. For example, it is contemplated that the cinacalcet Form III-based compositions may be used for treating a podocyte-related disease or disorder. In some embodiments, the podocyte-related disease is podocytopenia. In another aspect, the disease or disorder can manifest in an increase in the foot process width. In a further aspect, the podocyte-related disease or disorder can manifest as effacement or a decrease in slit diaphragm length. In another aspect, the podocyte-related disease or disorder can be a diminution of podocyte density. The podocyte-related disease may have resulted from a podocyte injury caused by, for example, mechanical stress, ischemia, lack of oxygen supply, a toxic substance, an endocrinologic disorder, an infection, a contrast agent, a mechanical trauma, a cytotoxic agent, a medication, an inflammation, radiation, an infection, a dysfunction of the immune system, a genetic disorder, an organ failure, an organ transplantation, or uropathy. In other aspects, the podocyte-related disease or disorder can be due to an abnormal expression or function of nephrin, podocin, FAT-1, CD2AP, Neph1, integrins, integrin-linked kinase, secreted protein acid rich in cysteine, Rho GTPases, actinin-4, synaptopodin, cyclin-dependent kinase5, podocalyxin, hic-5, GLEPP, TRPC6, dendrin, desmin, snail, notch, synaptopodin, HSP27, lamb4, podocalyxin, NHERF2, Ezrin, dystroglycans, 31 integrin collagen type 4 or Wnt-4. In another aspect, the podocyte related disease or disorder can be proteinuria, such as for example, microalbumiuria or macroalbumiuria. In a further aspect, the podocyte disease can be tubular atrophy.

Another kidney-related disorder that may be treated with the compositions of the present invention is polycystic kidney disease.

In still further embodiments, the cinacalcet Form III compositions of the invention may be used for the treatment of vascular calcification. Vascular calcification is an important and potentially serious complication of chronic renal failure. Two distinct patterns of vascular calcification have been identified (Proudfoot, D & Shanahan, C. Herz 26: 245-51, 2001), and it is common for both types to be present in uremic patients (Chen, N. & Moe, S. Semin Nephrol 24: 61-8, 2004). The first, medial calcification, occurs in the media of the vessel in conjunction with a phenotypic transformation of smooth muscle cells into osteoblast-like cells, while the other, atherogenesis, is associated with lipid-laden macrophages and intimal hyperplasia. Incorporated herein by reference in its entirety is U.S. Patent Application Publication No. 2006276534. The aforementioned application, provides exemplification of methods of detection and monitoring of various types of vascular calcification. Such methods may readily be used with the present invention to test for the efficacy and use of the cinacalcet Form III compositions in treating vascular calcification. In exemplary embodiments, the compositions of the present invention may be used to treat medial wall calcification, atherosclerotic calcification, occlusive arterial disease (also referred to as calciphylaxis or calcific uremic arteriolopathy). "Vascular calcification," as used herein, means formation, growth or deposition of extracellular matrix hydroxyapatite (calcium phosphate) crystal deposits in blood vessels. Vascular calcification encompasses coronary, valvular, aortic, and other blood vessel calcification. The term includes atherosclerotic and medial wall calcification.

In the treatment of vascular calcification, the cinacalcet Form III compositions may be combined with any agent typically used for the therapeutic intervention of vascular calcification. Such agents include, but are not limited to, other calcimimetics, including other forms of cinacalcet. For example, calcimimetic compounds that could be used include, but are not limited to those disclosed in, for example, European Patent No. 933 354 and 1 235 797; International Publication Nos. WO 01/34562, WO 93/04373, WO 94/18959, WO 95/11221, WO 96/12697, WO 97/41090; U.S. Pat. Nos. 5,688,938, 5,763,569, 5,962,314, 5,981,599, 6,001,884, 6,011,068, 6,031,003, 6,172,091, 6,211,244, 6,313,146, 6,342,532, 6,362,231, 6,432,656, 6,710,088, 6,908,935 and U.S. Patent Application Publication No. 2002/0107406 (each incorporated herein by reference). Additional compounds for use with cinacalcet Form III include, for example, vitamin D sterols and/or RENAGEL®.

In still additional embodiments, the compositions of the invention may be used to treat or prevent inflammatory bowel disease, irritable bowel syndrome and other bowel disorders such as, for example, lymphocytic colitis, collagenous colitis, diversion colitis, endometriosis, caustic enema-induced colitis, drug-induced ischemic colitis, NSAID-induced ulcers, nonspecific ulcers, stercoral ulcer, solitary rectal ulcer, typhilitis, colitis cystica profunda, pneumatosis cystoides intestinalis, and malakoplakia.

In the treatment of bowel-related disorders, the cinacalcet Form III may be combined with one or more other calcimimetics and/or one or more other agents used for the treatment of such bowel disease. For example, the cinacalcet Form III may be combined with one or more other medical treatments. For example, for patients with constipation-predominant IBS, osmotic laxatives can be used to effect defecation. These laxatives include hypertonic salt solution such as milk of magnesia, poorly absorbable sugars such as lactulose and sorbitol, and isotonic electrolyte solutions containing polyethylene glycol. For diarrhea-predominant IBS, opiate-based agents can be used, such as loperamide, Imodium, bile acid-sequestering drugs, acid-suppressing drugs in the $H_2$ receptor agonist and proton pump inhibitor classes. For pain-predominant IBS, methods of the invention can be practiced together with coadministration of anti-spasmodic agents, such as drugs that block cholinergic nerve function (e.g., dicyclomine, prifinium, cimetropiuim, zamifenacin), agents that prevent calcium flux (e.g., dilatiazem, pinaverium, octylonium, peppermint oil), and direct gut smooth muscle relaxants, as well as agents that act via unknown pathways. Other antispasmodics include mebeverine and trimebutine. In another aspect, cinacalcet Form III compounds and compositions of the invention can be used in the treatment of IBS with antidepressant agents, for example, agents in the tricyclic class, such as amitriotyline, trimipramine, desipramine, nortrioty-line, fluphenazine; the selective serotonin reuptake inhibitors, e.g., paroxetine, citalopram, mianserin; or serotonin receptor antagonists, e.g., ondansertron, granisetron, alosertron, or $5HT_4$ receptor antagonist SB-207266-A.

In yet another embodiment, the cinacalcet Form III compositions may be used for treating bowel disease in conjunction with other medications, for example, prokinetic medications, such as tegaserod, peripheral dopamine receptor antagonists, such as domperidone; hormonal treatments (for example, gonadotropin-releasing hormone, such as leuprolide; tranquilizers, such as phenaglycodol, meprobamate, heteronium plus amobarbital, propantheline plus phenobarbital, chlordiazepoxide, diazepam, medazepam, and alprazolam. In another aspect, the invention provides methods for treating bowel disease in conjunction with other medications, such as agents that blunt visceral hyperalgesia in bowel disease, for example, kappa-opioid compounds, $\alpha_2$-adrenoceptor agonists (e.g., yohimbine, lidamidine), neurokinin-1 ($NK_1$) receptor antagonists, somatostatin analogs (e.g., octreotide), or oxytocin. In a further aspect, methods of the invention can be practiced in conjunction with psychological therapy, cognitive therapy, biofeedback and stress reduction techniques, and hypnosis. In one aspect, compounds and compositions of the invention can be used in conjunction with itopride, saredutant, renzapride, lubiprostone, or dynogen.

The cinacalcet Form III compositions of the invention also may be used in treating disorders of intestinal fluid balance, secretion and absorption. In this regard, incorporated herein by reference in its entirety is PCT Publication No. WO 2007/027548, which provides a teaching of methods for modulating intestinal fluid balance. In specific embodiments, the cinacalcet Form III compositions of the invention may be used in the treatment of diarrhea or other disorders that manifest as an abnormal intestinal motility. The diarrhea may be an osmotic, secretory, exudative or rapid transit diarrhea. It may be acute or chronic. It may be caused by exposure to one or more of a variety of infective agents (e.g., *E. coli, Shigella, Salmonella, Campylobacter jejuni, Vibrio cholera*, cholera toxin, El tor, Giardiasis, *Entamoeba histolyca, cryptosporidium parvum*, Norfolk viruses, Rotaviruses, Adenoviruses Caliciviruses, Astroviruses or Enteroviruses). The diarrhea may be caused by an alteration in cAMP or cGMP or as a result of exposure to antibiotics, anti-inflammatory agents, caffeine, steroids, drugs, laxatives and the like. The diarrhea also may be caused by malabsorption or maldigestion. In still other embodiments, it may be caused by lactase deficiency or short bowel syndrome. Diarrhea also may be due to gastrointestinal surgery, e.g., abdominal procedure or caused by chemotherapy, radiation treatment, inflammation or toxic traumatic injury.

In treating a disorder of intestinal fluid balance, the cinacalcet Form III compositions of the invention may be combined with one or more other agents typically used for such disorders, e.g., anti-diarrheal agents.

In any of the combination therapies, be they for the treatment of HPT, carcinoma or other hypercalcemia-related disorder, the polymorph may be administered concurrently or sequentially with the second agent with which it is being combined.

The method of treatment will comprise administering to a patient in need thereof, concurrently or sequentially, a therapeutically effective amount of (a) at least the polymorph III disclosed herein, and (b) the second therapeutic agent with which the patient is being treated. For example, for the treatment of carcinoma, the second therapeutic agent will be an antineoplastic agent as discussed above. Where the condition being treated is HPT, the second therapeutic agent may be e.g., vitamin D, a calcium binding agent or the like.

The amount and frequency of administration of the polymorph of the invention and the second therapeutic agent (e.g., chemotherapeutic agents and/or radiation therapy and/or other agent for treating hypercalcemia) will be regulated according to the judgment of the attending clinician (physician) considering such factors as age, condition and size of the patient as well as severity of the disease being treated. A dosage regimen of the inventive polymorph can be oral administration of from 10 mg to 2000 mg/day, 10 to 1000 mg/day, 10 to 600 mg/day, from about 10 mg to about 300 mg/day in one, two, three or four divided doses, to lower iPTH and/or serum calcium levels as discussed above. Intermittent therapy (e.g., one week out of three weeks or three out of four weeks) may also be used.

The second therapeutic agent can be administered according to therapeutic protocols well known in the art. It will be apparent to those skilled in the art that in cancer therapy, the administration of the vitamin D steroid or chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

As noted above, the methods of this invention, the inventive polymorph is administered concurrently or sequentially with a second therapeutic agent. Thus, it is not necessary that, for example, the second therapeutic agent and the polymorph, should be administered simultaneously or essentially simultaneously.

Furthermore, in general, the inventive polymorph and the second therapeutic agent do not have to be administered in the same pharmaceutical composition, and may, because of different physical and chemical characteristics, have to be administered by different routes. For example, the inventive polymorph may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of a polymorph/second therapeutic agent combination will depend upon the diagnosis of the attending physicians and their judgment of the condition of the patient and the appropriate treatment protocol.

Where the polymorph, and the second therapeutic agent are not administered simultaneously or essentially simultaneously, the order of administration of the polymorph, and the second therapeutic agent, may not be important. Thus, the inventive polymorph may be administered first, followed by the administration of the second therapeutic agent (e.g., chemotherapeutic agent and/or radiation); or the second therapeutic agent may be administered first, followed by the administration of the polymorph. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

The practicing physician can modify each protocol for the administration of a component (therapeutic agent—i.e., the inventive polymorph, and the second therapeutic agent—e.g., a chemotherapeutic agent or radiation) of the treatment according to the individual patient's needs, as the treatment proceeds. The attending clinician, in judging whether treatment is effective at the dosage administered, will consider the general wellbeing of the patient as well as more definite signs such as relief of disease-related symptoms, e.g., anxiety, depression, nausea, vomiting, bone fractures, kidney stones as well as monitoring the iPTH, serum calcium levels, serum phosphorus levels, monitoring the subject for a dynamic bone disease (e.g., using standard Nichols IRMA). Relief of disease-related symptoms and improvement in overall condition can also be used to help judge effectiveness of treatment.

In certain embodiments, the present invention provides kits for administering a the polymorph of the invention, which kit comprises, in a container, the polymorph composition, instructions and instruments for administration of the polymorph. The kit also may optionally comprise one or more additional components, such as for example, additional therapeutic compositions, pharmaceutical carriers or diluents for mixing the polymorph prior to administration, assay components for determining the efficacy of the polymorph (e.g., assay components for determining the level of iPTH, serum calcium, serum phosphorus and the like), instruments for obtaining serum to test for the efficacy of the polymorph and the like.

EXAMPLES

The following examples are intended to be illustrative rather than limiting.

Example 1

Polymorph III may be obtained in the following manner. Sublimation of Form I leads to formation of Form III. Sublimation was carried out on the Form I material on a laboratory scale using a cold finger sublimation apparatus. The apparatus was immersed in a silicone oil bath and the cold finger was water-cooled. The system was sealed under vacuum. Vacuum was not released until the final solids were harvested. The solids were observed through optical microscopy and characterized by XRPD analysis.

Example 2

The characterization of the crystals produced in example 1 proceeded as follows.

A colorless plate of $C_{22}H_{23}ClF_3N$ having approximate dimensions of 0.45×0.35×0.13 mm was mounted on a glass fiber in random orientation. Preliminary examination and data collection were performed with Mo Kα radiation (λ=0.71073 Å) on a Nonius KappaCCD diffractometer. Refinements were performed on a LINUX PC using SHELX97 (Sheldrick, G. M., *SHELX97, A Program for Crystal Structure Refinement*, University of Gottingen, Germany (1997)). The crystallographic drawings were obtained using programs ORTEP (Johnson, *J Appl Cryst* 30:565 (1997)), CAMERON (Watkin et al., *Chemical Crystallography Laboratory*, University of Oxford: Oxford (1996)), and Mercury (Bruno et al., *Acta Crystallogr.* B58:389 (2002)).

Cell constants and an orientation matrix for data collection were obtained from least-squares refinement using the setting angles of 10737 reflections in the range 2°<θ<25°. The refined mosaicity from DENZO/SCALEPACK (Otwinowski et al., *Methods Enzymol* 276:307 (1997)) was 1.17° indicating poor crystal quality. The space group was determined by the program XPREP (Bruker, *XPREP in SHELXTL version* 6.12, Bruker AXS, Inc. Madison, Wis.: USE (2002)). There were no systematic absences; the space group was determined to be P1 (no. 1).

The data were collected to a maximum 2θ value of 50.18°, at a temperature of 150±1 K. Frames were integrated with DENZO-SMN (Otwinowski et al., *Methods Enzymol* 276: 307 (1997)).

A total of 10737 reflections were collected, of which 6229 were unique. Lorentz and polarization corrections were applied to the data. The linear absorption coefficient was 2.13 cm$^{-1}$ for Mo Kα radiation. An empirical absorption correction using SCALEPACK (Otwinowski et al., *Methods Enzymol* 276:307 (1997)) was applied. Transmission coefficients ranged from 0.883 to 0.974. Intensities of equivalent reflections were averaged. The agreement factor for the averaging was 13.8% based upon intensity.

The structure of Form III was solved by direct methods using SIR2004 (Burla et al., *J Appl Cyst* 38:381 (2005)). The remaining atoms were located in succeeding difference Fourier syntheses. Hydrogen atoms were included in the refinement but restrained to ride on the atom to which they are bonded. The structure was refined in full-matrix least squares by minimizing the function:

$$\Sigma w(|F_o|^2 - |F_c|^2)^2$$

The weight w is defined as $1/[\sigma^2(F_o^2)+(0.0981P)^2+(0.8406P)]$, where $P=(F_o^2+2F_c^2)/3$.

Scattering factors were taken from the "International Tables for Crystallography," vol. C, Kluwer Academic Publishers: Dordrecht, The Netherlands (1992), Tables 4.2.6.8 and 6.1.1.4. Of the 6229 reflections used in the refinements, only the reflections with $F_o^2>2\sigma(F_o^2)$ were used in calculating R. A total of 4198 reflections were used in the calculations. The final cycle of refinement included 490 variable parameters and converged (largest parameter shift was equal to its estimated standard deviation) with unweighted and weighted agreement factors of:

$$R = \sum |F_o - F_c|/\sum F_o = 0.086$$

$$R_w = \sqrt{(\sum w(F_o^2 - F_c^2)^2/\sum w(F_o^2)^2)} = 0.188$$

The standard deviation of an observation of unit weight was 1.03. The highest peak in the final difference Fourier had a height of 0.31 e/Å$^3$. The minimum negative peak had a height of −0.33 e/Å$^3$. The factor for the determination of the absolute structure (Flack, *Acta Cryst* A39:876 (1983)) refined to 0.2 (1).

Figure 1:
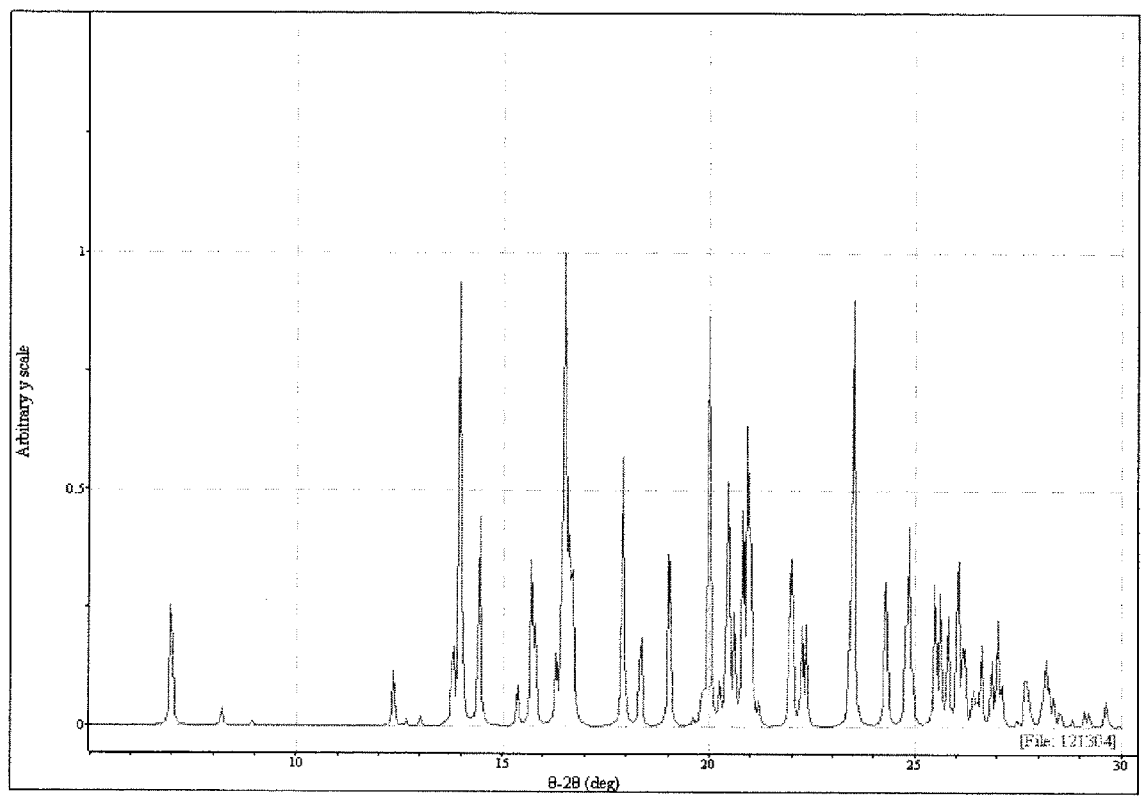
FIG. 1 shows the calculated XRPD pattern of form III of cinacalcet hydrochloride.

A calculated XRPD pattern (FIG. 1) was generated for Cu radiation using PowderCell 2.3 and the atomic coordinates, space group, and unit cell parameters from the single crystal data. FIG. 1

Packing diagrams were prepared using CAMERON (Watkin et al., *Chemical Crystallography Laboratory*, University of Oxford: Oxford (1996)) modeling software. Hydrogen bonding is represented as dashed lines. Additional figures were generated using Mercury 1.3 modeling software.

Figure 2:
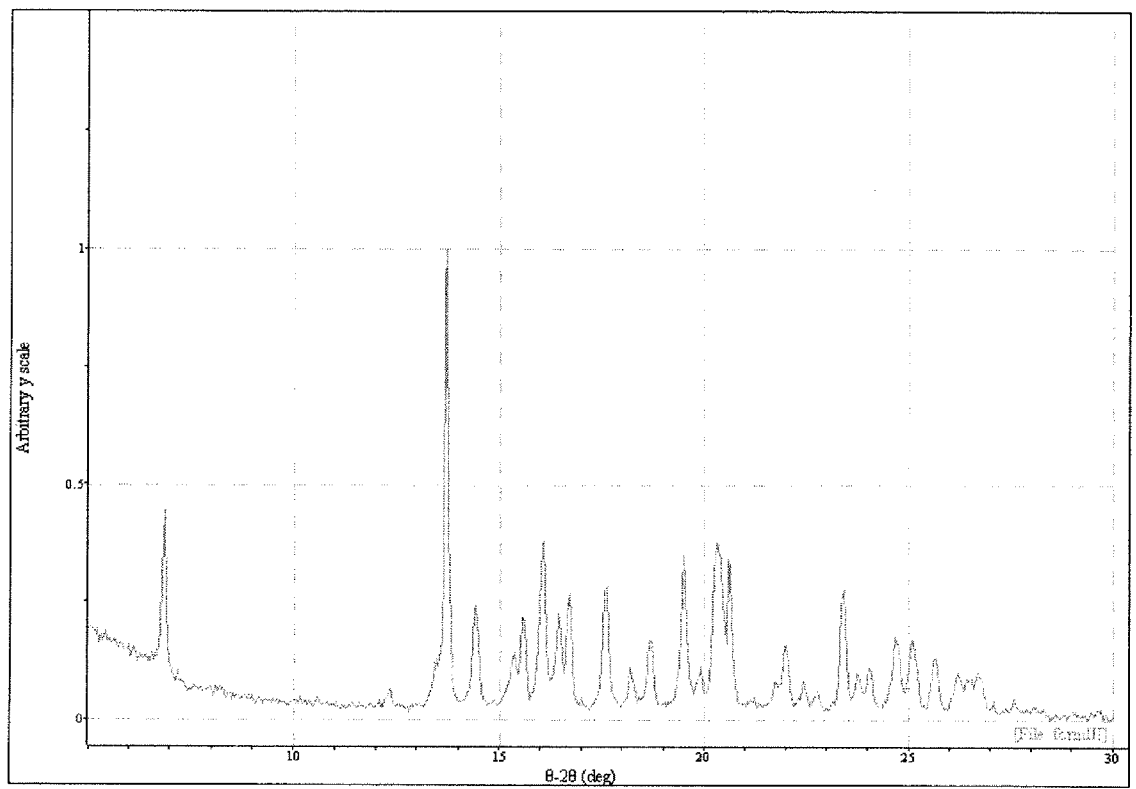
FIG. 2 shows the experimental XRPD pattern of form III of cinacalcet hydrochloride.
Figure 3:
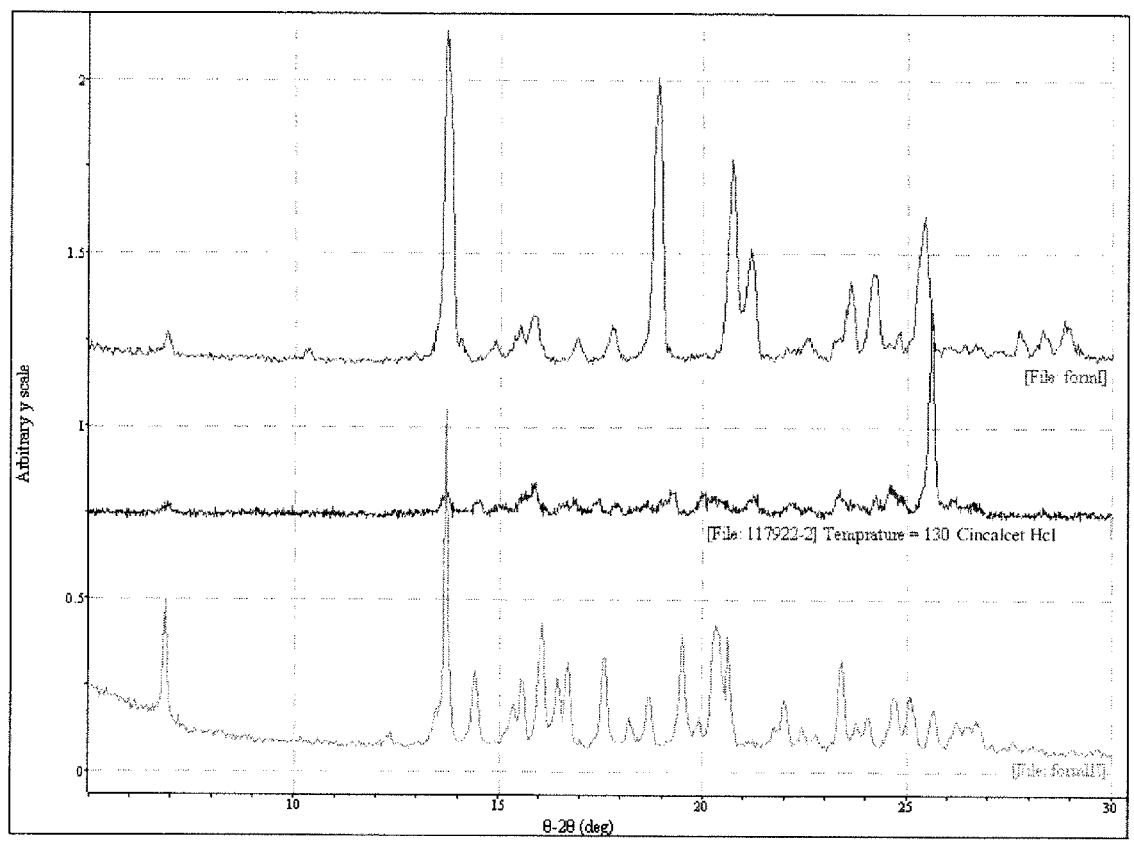
FIG. 3 shows experimental XRPD comparisons of form I (top trace), mixture of Form I and Form III (middle trace), and Form III (bottom trace).

X-ray powder diffraction (XRPD) analysis was performed (FIG. 2 and FIG. 3) using an Inel XRG-3000 diffractometer equipped with a CPS (Curved Position Sensitive) detector with a 2θ range of 120°. Real time data were collected using Cu—Kα radiation starting at approximately 4°2θ at a resolution of 0.03+2θ. The tube voltage and amperage were set to 40 kV and 30 mA, respectively. The monochromator slit was set at 5 mm by 160 μm. The pattern is displayed from 2.5-40°2θ. Samples were prepared for analysis by packing them into 1 mm thin-walled glass capillaries. Each capillary was mounted onto a goniometer head that was motorized to permit spinning of the capillary during data acquisition. The samples were analyzed for 5 min. Instrument calibration was performed using a silicon reference standard. FIG. 2 shows the measured XRPD pattern for Form III, and FIG. 3 shows a comparison of XRPD patterns of pure Form I (top), a mixture of Form I and Form III (middle), and pure Form III cinacalcet hydrochloride.

The XRPD pattern of Form III showed the following major diffraction lines (°2θ): 12.3402, 14.4334, 15.3545, 16.443, 16.6942, 17.6152, 18.2013, 18.6618, 19.4992, 19.9178, 20.2946, 20.5877, 21.7599, 21.9692, 22.4297, 24.0206, and 25.0672.

The triclinic cell parameters and calculated volume are: a=7.178 (4), b=11.367 (4), c=13.712 (5) Å, α=71.546 (15), β×77.004 (17), γ=87.93 (2)°, V=1033.3 (7) Å$^3$. For Z=2 and a formula weight of 393.88, the calculated density is 1.266 g/cm$^3$. The space group was determined to be P1. A summary of the crystal data and crystallographic data collection parameters are provided in Table 1 presented at the end of this specification.

Usually R-values in the range of 0.02 to 0.06 are quoted for the most reliably determined structures (Glusker et al. *Crystal Structure Analysis: A Primer*, 2$^{nd}$ Ed., Oxford University Press: New York, 1985, p. 97). While the R-value of 0.086 (8.6%) is outside of the indicated range, the structure is considered of sufficient quality to resolve the structure but not sufficient resolution to resolve the absolute stereochemistry of the molecule.

Figure 4:
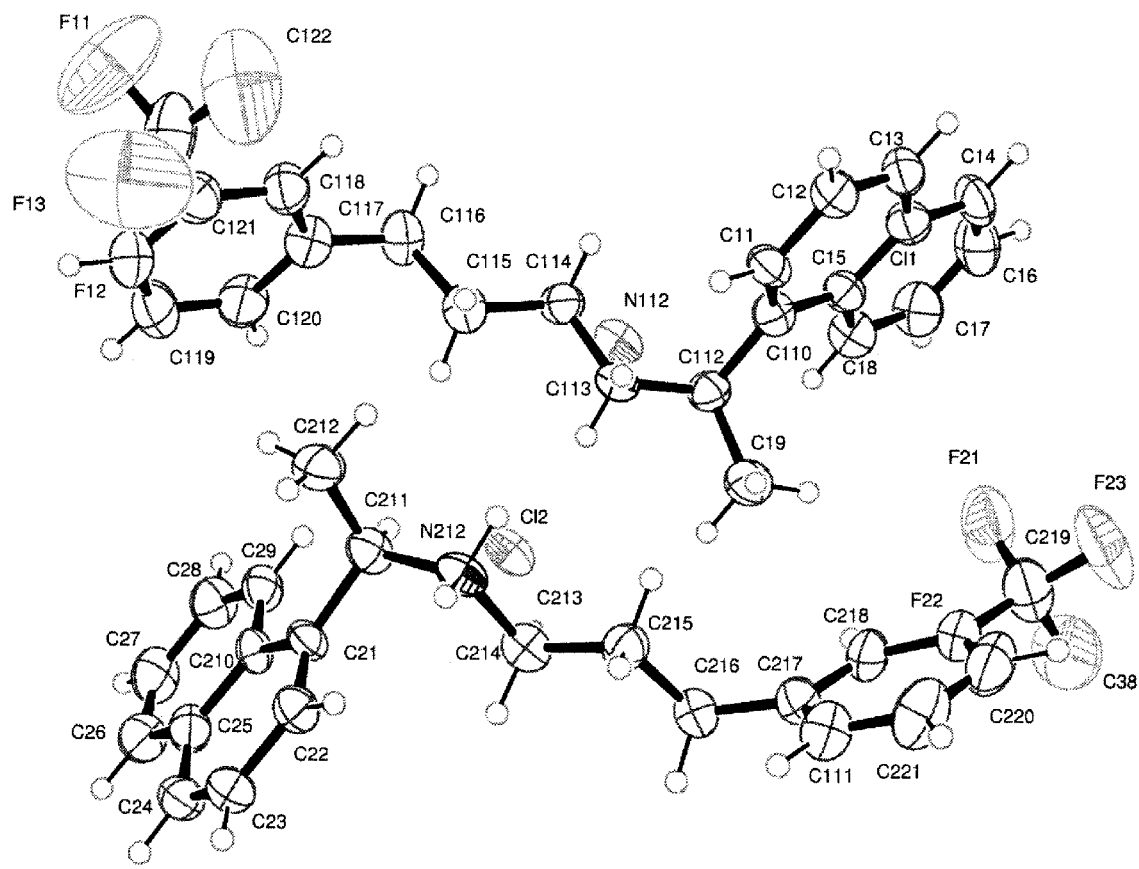
FIG. 4 shows an ORTEP drawing of cinacalcet HCl Form III. Atoms are represented by 50% probability anisotropic thermal ellipsoids.

An ORTEP [Johnson, *J. Appl. Cryst.* 1997, 30, 565] drawing of cinacalcet HCl Form III is shown in FIG. 4. The single crystal structure is the same as the proposed structure seen in FIG. 5. The asymmetric unit shown in FIG. 5 contains two molecules and the corresponding chloride anions. The crystallography confirms the material is a stoichiometric salt.

Figure 6:
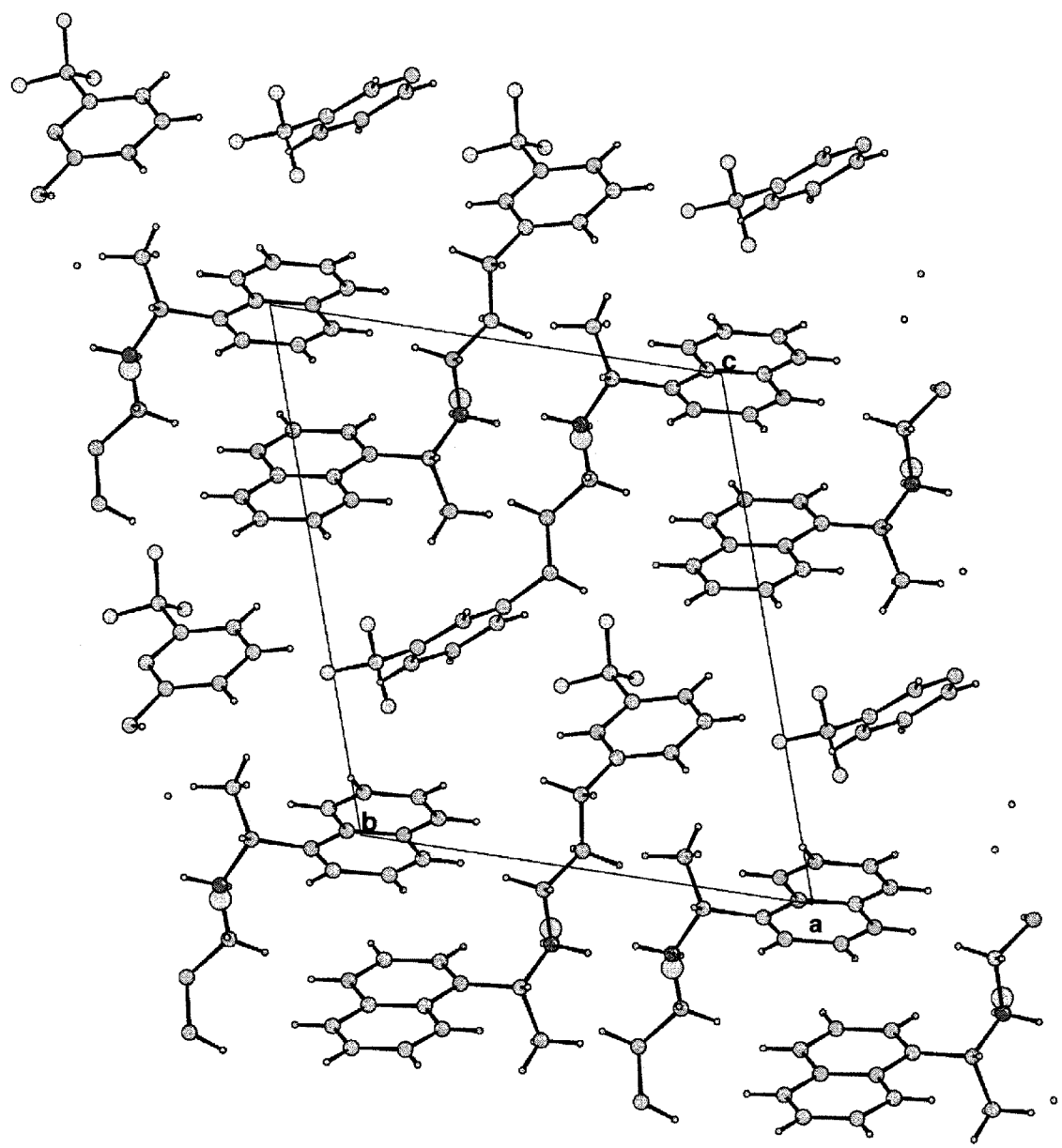
FIG. 6 shows the packing diagram of cinacalcet Form III viewed down the crystallographic a-axis.
Figure 7:
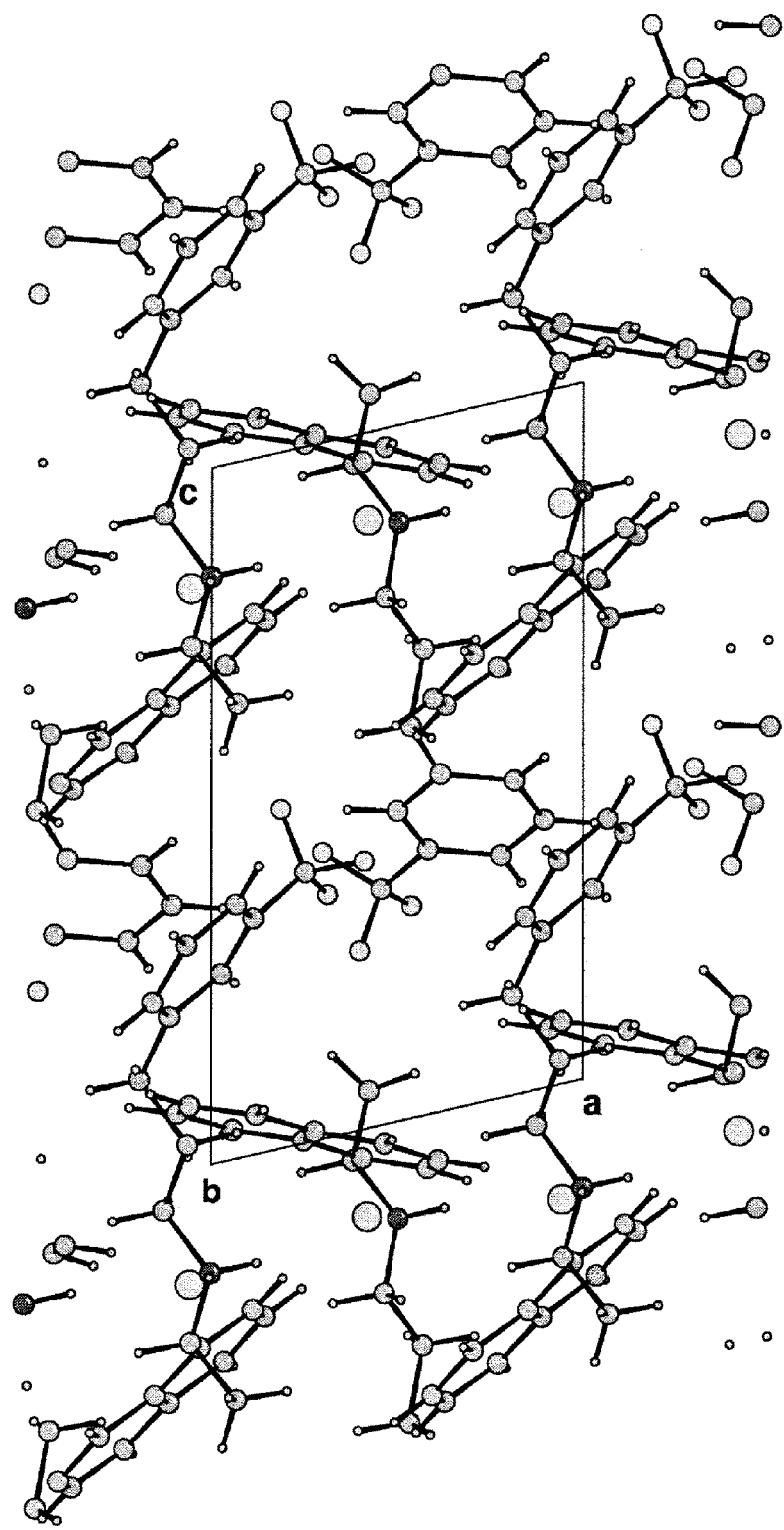
FIG. 7 shows the packing diagram of cinacalcet Form III viewed down the crystallographic b-axis.
Figure 8:
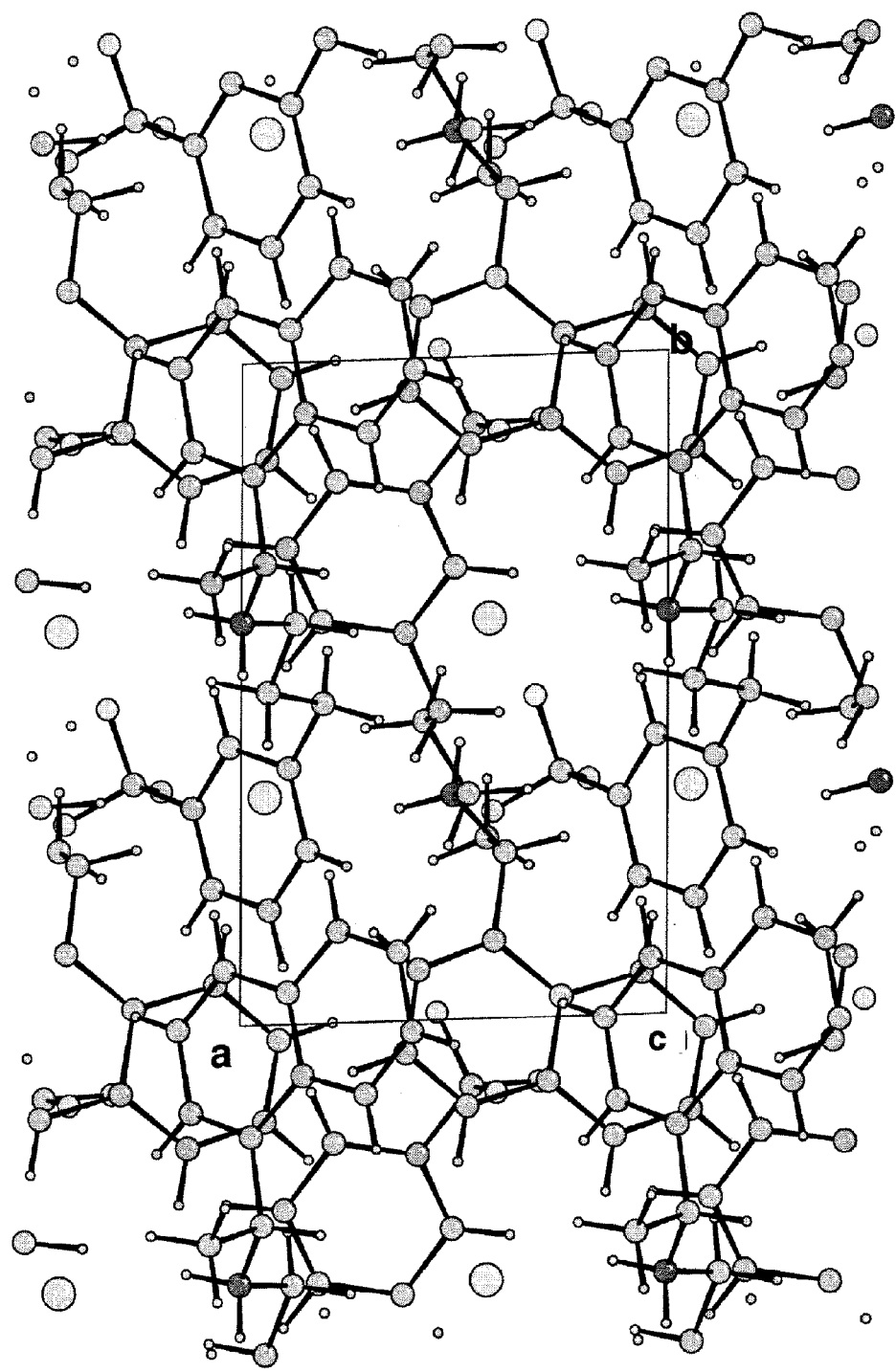
FIG. 8 shows the packing diagram of cinacalcet Form III viewed down the crystallographic c-axis.
Figure 9:
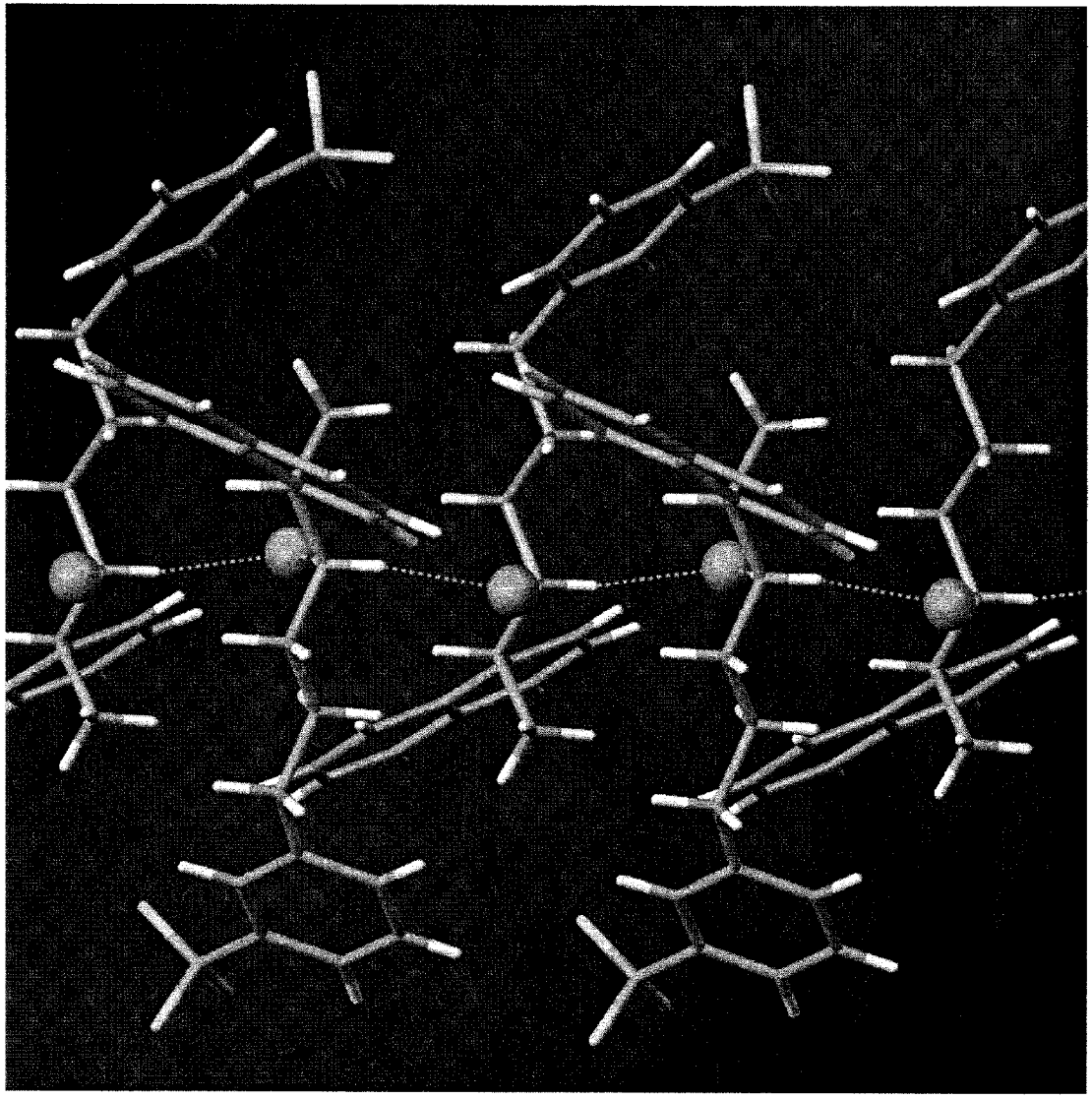
FIG. 9 shows the hydrogen bonding network for cinacalcet Form III. The hydrogen bonds are represented as dashed blue lines.

Packing diagrams viewed along the a, b, and c crystallographic axes are shown in FIGS. 6-8 respectively. The hydrogen atoms are shown in these figures. The hydrogen bonding interactions between the molecule occurs between the protonated amine (N112 and N212) and the chloride ions Cl1 and Cl2. The chloride ions exhibit two interactions with the neighboring amine protons with Cl N hydrogen bonding interactions of approximately 3.15 Å. A view of the one dimensional hydrogen bonding network observed in cinacalcet HCl Form III is shown in FIG. 9.

Figure 10A:
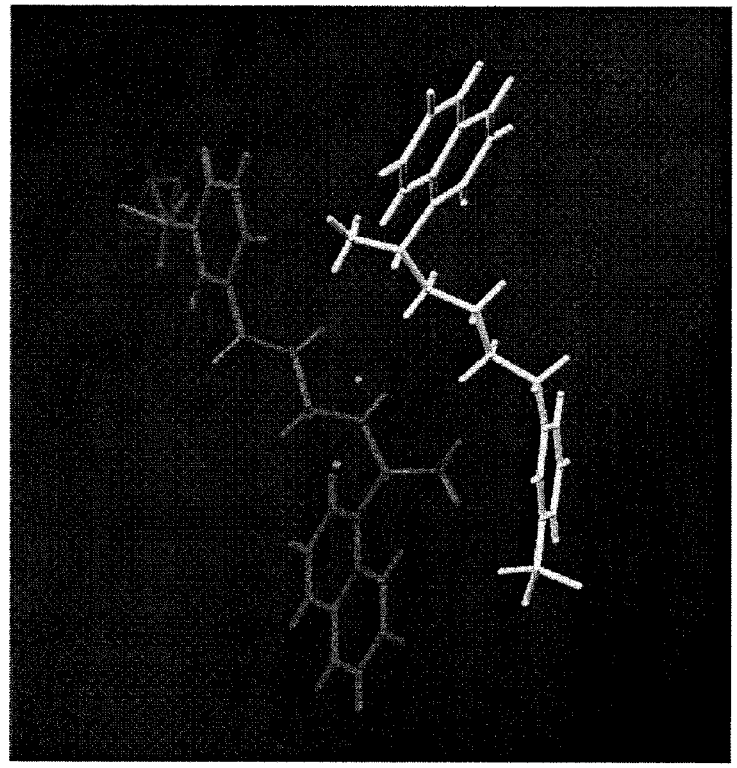
FIG. 10A-10B show the overlay of the cinacalcet Form I molecule (blue) with the two cinacalcet molecules (red and yellow) in the Form III crystal structure.
Figure 10B:
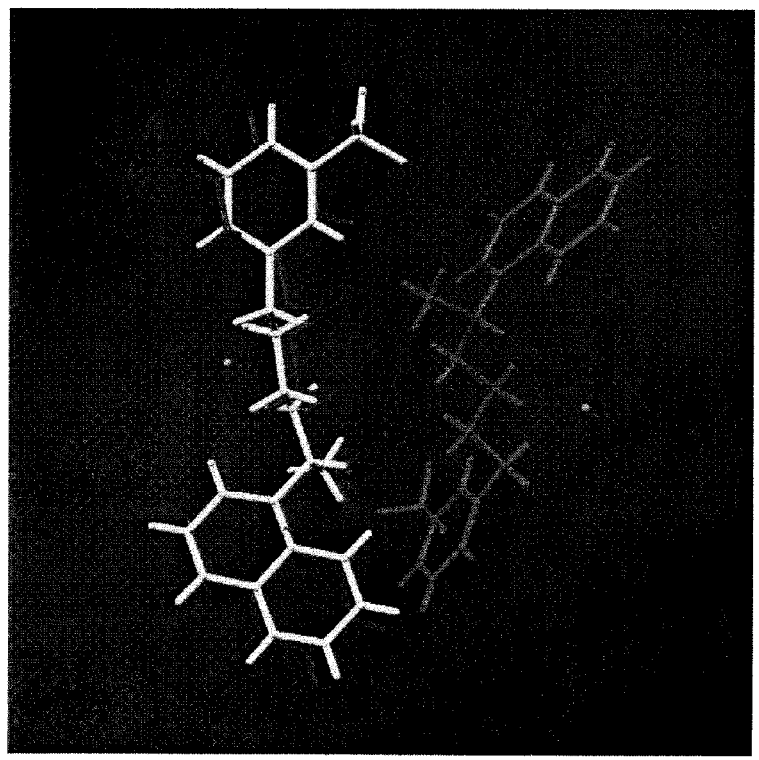
Figure 11:
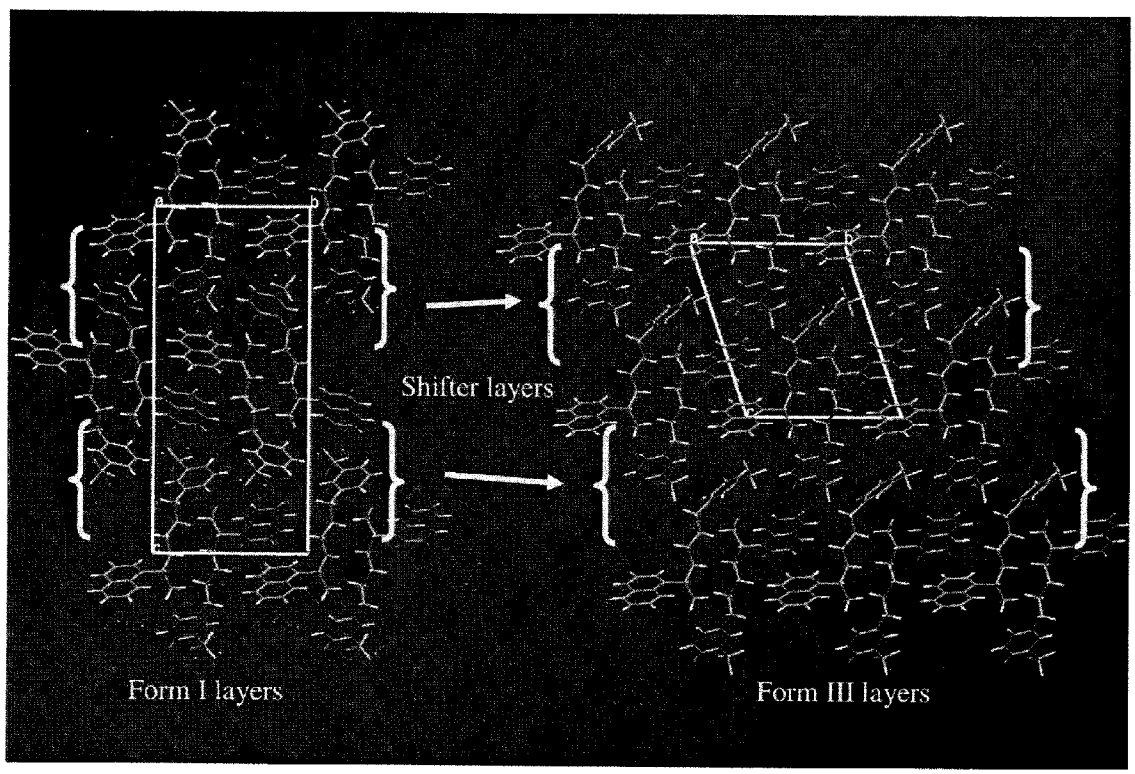
FIG. 11 shows a view of the packing diagram of Form I and Form III viewed down the crystallographic a-axis.

A comparison of the molecule from the Form I and Form III crystal structures are shown in FIG. 10. The Form I molecule has a very reasonable overlap with one Form III molecule, but the trifluoromethyl group on the second Form III molecule is rotated approximately 180° with respect to the Form I molecule. As shown in FIG. 11, the packing of Form I and Form II are very similar, but the rotation of the trifluoromethyl group shifts the stacking on the layers in the Form III crystal structure.

FIG. 1 shows a calculated XRPD pattern of cinacalcet HCl Form III, generated from the single crystal data. The experimental XRPD pattern of cinacalcet HCl Form III is shown in FIG. 2. A comparison of the calculated XRPD pattern to the experimental pattern of cinacalcet HCl Form III is shown in FIG. 3. All peaks in the experimental patterns are represented in the calculated XRPD pattern, indicating the bulk material is likely a single phase. The slight shifts in peak location are likely due to the fact that the experimental powder pattern was collected at ambient temperature, and the single crystal data was collected at 150 K. Low temperatures are used in single crystal analysis to improve the quality of the structure. To test this hypothesis, the Form III and Form I crystals were indexed at room temperature and the unit cell data is summarized in Table 2. The comparison of the calculated XRPD pattern with the room temperature unit cell data for cinacalcet HCl. The comparison of the calculated XRPD pattern with the room temperature unit cell data for cinacalcet HCl Form III and Form I show much better agreement with their respective experimental patterns.

The absolute configuration of the molecule can be determined by analysis of anomalous X-ray scattering by the crystal. The differences in intensities of the anomalous scattering are then compared with calculated scattering intensities for each enantiomer. These measured and calculated intensities can then be fit to a parameter, the Flack factor [Flack and Bernardinelli, *Acta Cryst.* 1999, A55, 908; Flack and Bernardinelli, *J. Appl. Cryst.* 2000, 33, 1143]. After a structure is solved the quality of the data should be assessed for its inversion-distinguishing power, this is done be an examination of the standard uncertainty of the Flack parameter. For cinacalcet HCl Form III, the standard uncertainty, (u), equals 0.1, which is classified as sufficient/weak inversion-distinguishing power. An error of this magnitude means that a priori biological, chemical or physical evidence is required to show that the compound is truly enantiopure, and to prove that the absolute structure determination is valid. The Flack factor, x(u) should be close to 0 if the configuration of the solved structure is correct, within statistical fluctuations, usually |x|<2u. x will be close to 1 if the inverse model is correct. The measured Flack factor for the structure of cinacalcet HCl Form III shown in FIG. 4 is 0.2 with a standard uncertainty of 0.1 (Table 1). Therefore, the absolute configuration of the model in FIG. 4 is correct. This structure contains one chiral center located at C211 (refer to FIG. 4, ORTEP drawing). Cinacalcet HCl Form III has been assigned as R configuration (SSCI notebook reference 2163-08). This is consistent with the proposed configuration in FIG. 5.

Further characterization of the new polymorph of the present invention is presented in the tables of positional parameters and their estimated standard deviations (Table 3 below), anisotropic temperature factor coefficients (Table 4 below), bond distances (Table 5 below), bond angles (Table 6 below) and torsion angles (Table 7 below).

The data presented herein show a single crystal structure of cinacalcet HCl Form III that was determined to confirm the molecular structure of cinacalcet. The space group was determined to be P1 (no. 1). The structure of cinacalcet HCl Form III consists of molecules hydrogen bonding to the chloride ions resulting in a one dimensional chain running along the crystallographic a-axis. All peaks in the experimental patterns were represented in the calculated XRPD pattern, but significant shifting the calculated XRPD pattern was observed. The Form I and Form III crystals were indexed at room temperature and the calculated XRPD patterns generated with the room temperature data were in agreement with the experimental patterns, indicating the bulk materials were most likely a single phase.

Tables of Characterization Data

TABLE 1

| Crystal Data and Data Collection Parameters for Cinacalcet HCl polymorph III | |
|---|---|
| formula | $C_{22}H_{23}ClF_3N$ |
| formula weight | 393.88 |
| space group | P1 (No. 1) |
| a, Å | 7.178(4) |
| b, Å | 11.367(4) |
| c, Å | 13.712(5) |
| a, deg | 71.546(15) |
| b, deg | 77.004(17) |
| g, deg | 87.93(2) |
| V, Å$^3$ | 1033.3(7) |
| Z | 2 |
| $d_{calc}$, g cm$^{-3}$ | 1.266 |
| crystal dimensions, mm | 0.45 × 0.35 × 0.13 |
| temperature, K. | 150. |
| radiation (wavelength, Å) | Mo K$_a$ (0.71073) |
| monochromator | graphite |
| linear abs coef, mm$^{-1}$ | 0.213 |
| absorption correction applied | empirical[a] |
| transmission factors: min, max | 0.883, 0.974 |
| diffractometer | Nonius KappaCCD |
| h, k, l range | −8 to 7 −13 to 13 −16 to 16 |
| 2θ range, deg | 3.21-50.18 |
| mosaicity, deg | 1.17 |
| programs used | SHELXTL |
| F$_{000}$ | 412.0 |
| weighting | $1/[\sigma^2(F_o^2) + (0.0981P)^2 + 0.8406P]$ where $P = (F_o^2 + 2F_c^2)/3$ |
| data collected | 10737 |
| unique data | 6229 |
| R$_{int}$ | 0.138 |
| data used in refinement | 6229 |
| cutoff used in R-factor calculations | $F_o^2 > 2.0\sigma(F_o^2)$ |
| data with I > 2.0σ(I) | 4198 |
| refined extinction coef | 0.0600 |
| number of variables | 490 |
| largest shift/esd in final cycle | 0.00 |
| R(F$_o$) | 0.086 |
| R$_w$(F$_o^2$) | 0.188 |
| goodness of fit | 1.033 |
| absolute structure determination | Flack parameter[b] (0.2(1)) |

[a] Otwinowski Z. & Minor, W. Methods Enzymol., 1997, 276, 307.
[b] Flack, H. D. Acta Cryst., 1983 A39, 876.

TABLE 2

Room Temperature Unit Cell data for Cinacalcet HCl Form I and Form III

| | Form I 170 K Cell | Form I 298 K Cell | Form III 150 K Cell | Form III 298 K Cell |
|---|---|---|---|---|
| space group | $P2_12_12_1$ (No. 19) | $P2_12_12_1$ (No. 19) | P1 (No. 1) | P1 (No. 1) |
| a, Å | 7.18100(10) | 7.170 | 7.178(4) | 7.211 |
| b, Å | 11.3448(2) | 11.364 | 11.367(4) | 11.395 |
| c, Å | 25.3576(4) | 25.487 | 13.712(5) | 13.881 |
| a, deg | 90 | 90 | 71.546(15) | 70.89 |
| b, deg | 90 | 90 | 77.004(17) | 78.88 |
| g, deg | 90 | 90 | 87.93(2) | 88.38 |
| V, Å³ | 2065.81(10) | 2076.5 | 1033.3(7) | 1056.8 |
| Z | 4 | 4 | 2 | 2 |
| temp K | 170 | 298 | 150 | 298 |

TABLE 3

Positional Parameters and Their Estimated Standard Deviations for Cinacalcet HCl Form III

| Atom | x | y | z | U(Å²) |
|---|---|---|---|---|
| Cl(1) | −0.5816(2) | −0.39479(16) | 0.87376(15) | 0.0452(7) |
| Cl(2) | −0.0553(2) | −0.65521(16) | 0.83424(15) | 0.0461(7) |
| F(11) | 0.3108(15) | −0.5138(9) | 1.3493(9) | 0.166(5) |
| F(12) | 0.4089(14) | −0.6864(12) | 1.3852(11) | 0.199(7) |
| F(13) | 0.1854(13) | −0.6410(12) | 1.4871(7) | 0.167(5) |
| F(21) | 0.5375(10) | 0.0122(5) | 0.3055(6) | 0.111(3) |
| F(22) | 0.2973(10) | −0.0974(6) | 0.4112(5) | 0.104(3) |
| F(23) | 0.3971(12) | −0.1122(7) | 0.2581(6) | 0.117(3) |
| N(112) | −0.0009(8) | −0.3908(5) | 0.8440(4) | 0.037(2) |
| N(212) | 0.5024(9) | −0.6599(5) | 0.8608(5) | 0.040(2) |
| C(11) | −0.0268(12) | −0.1682(7) | 0.7410(6) | 0.042(3) |
| C(12) | 0.1138(11) | −0.1296(7) | 0.7777(6) | 0.042(3) |
| C(13) | 0.1448(13) | −0.0037(7) | 0.7644(6) | 0.051(3) |
| C(14) | 0.0376(13) | 0.0848(8) | 0.7134(6) | 0.051(3) |
| C(15) | −0.1108(11) | 0.0491(7) | 0.6726(6) | 0.046(3) |
| C(16) | −0.2286(14) | 0.1393(8) | 0.6206(7) | 0.059(3) |
| C(17) | −0.3700(14) | 0.1051(9) | 0.5838(7) | 0.066(4) |
| C(18) | −0.4043(13) | −0.0168(9) | 0.5967(7) | 0.061(4) |
| C(19) | −0.2948(11) | −0.1088(8) | 0.6473(6) | 0.050(3) |
| C(21) | 0.4045(11) | −0.8819(6) | 0.9592(6) | 0.034(3) |
| C(22) | 0.5823(11) | −0.9227(7) | 0.9233(6) | 0.044(3) |
| C(23) | 0.6110(13) | −1.0485(7) | 0.9310(6) | 0.047(3) |
| C(24) | 0.4650(12) | −1.1311(7) | 0.9726(6) | 0.044(3) |
| C(25) | 0.2770(12) | −1.0973(7) | 1.0132(6) | 0.045(3) |
| C(26) | 0.1215(13) | −1.1825(8) | 1.0558(6) | 0.051(3) |
| C(27) | −0.0579(14) | −1.1461(8) | 1.0907(7) | 0.058(3) |
| C(28) | −0.0907(13) | −1.0233(8) | 1.0837(6) | 0.052(3) |
| C(29) | 0.0579(11) | −0.9363(7) | 1.0422(6) | 0.042(3) |
| C(38) | 0.4550(16) | −0.1013(9) | 0.3398(8) | 0.071(4) |
| C(110) | −0.1471(11) | −0.0780(7) | 0.6871(6) | 0.039(2) |
| C(111) | −0.0530(12) | −0.3030(7) | 0.7509(6) | 0.040(3) |
| C(112) | 0.0696(12) | −0.3289(7) | 0.6545(6) | 0.049(3) |
| C(113) | −0.1256(12) | −0.3941(7) | 0.9490(6) | 0.041(3) |
| C(114) | −0.0627(12) | −0.4972(7) | 1.0353(6) | 0.045(3) |
| C(115) | −0.1912(13) | −0.5161(8) | 1.1442(6) | 0.051(3) |
| C(116) | −0.1112(12) | −0.6121(8) | 1.2259(6) | 0.050(3) |
| C(117) | 0.0271(14) | −0.5777(8) | 1.2702(6) | 0.052(3) |
| C(118) | 0.1122(12) | −0.6681(8) | 1.3395(6) | 0.054(3) |
| C(119) | 0.0662(17) | −0.7913(9) | 1.3653(7) | 0.074(4) |
| C(120) | −0.0664(18) | −0.8256(9) | 1.3227(8) | 0.079(4) |
| C(121) | −0.1558(16) | −0.7370(9) | 1.2521(7) | 0.063(4) |
| C(122) | 0.2504(16) | −0.6290(12) | 1.3887(9) | 0.080(5) |
| C(210) | 0.2473(10) | −0.9692(6) | 1.0041(5) | 0.034(2) |
| C(211) | 0.3794(12) | −0.7487(7) | 0.9593(6) | 0.042(3) |
| C(212) | 0.4222(14) | −0.7265(8) | 1.0539(6) | 0.056(3) |
| C(213) | 0.4664(11) | −0.6589(7) | 0.7579(6) | 0.040(3) |
| C(214) | 0.5705(12) | −0.5475(7) | 0.6713(6) | 0.044(3) |
| C(215) | 0.5347(13) | −0.5325(7) | 0.5650(6) | 0.047(3) |
| C(216) | 0.6158(12) | −0.4128(7) | 0.4854(6) | 0.046(3) |
| C(217) | 0.4995(14) | −0.3158(8) | 0.4463(6) | 0.051(3) |
| C(219) | 0.7790(15) | −0.1818(9) | 0.3483(7) | 0.067(4) |
| C(220) | 0.8949(14) | −0.2807(10) | 0.3853(7) | 0.066(4) |
| C(221) | 0.8145(13) | −0.3921(8) | 0.4518(7) | 0.057(3) |
| H(12) | 0.192 | −0.189 | 0.813 | 0.050 |
| H(13) | 0.243 | 0.020 | 0.792 | 0.061 |
| H(14) | 0.061 | 0.170 | 0.705 | 0.060 |
| H(16) | −0.207 | 0.225 | 0.612 | 0.070 |
| H(17) | −0.447 | 0.167 | 0.549 | 0.079 |
| H(18) | −0.505 | −0.039 | 0.570 | 0.073 |
| H(19) | −0.320 | −0.193 | 0.655 | 0.059 |
| H(22) | 0.688 | −0.865 | 0.893 | 0.053 |
| H(23) | 0.735 | −1.074 | 0.906 | 0.057 |
| H(24) | 0.486 | −1.215 | 0.975 | 0.052 |
| H(26) | 0.141 | −1.267 | 1.061 | 0.061 |
| H(27) | −0.161 | −1.206 | 1.120 | 0.070 |
| H(28) | −0.216 | −0.999 | 1.107 | 0.063 |
| H(29) | 0.034 | −0.852 | 1.039 | 0.051 |
| H(111) | −0.190 | −0.320 | 0.754 | 0.048 |
| H(117) | 0.063 | −0.493 | 1.253 | 0.062 |
| H(119) | 0.127 | −0.852 | 1.412 | 0.090 |
| H(11A) | 0.033 | −0.275 | 0.591 | 0.074 |
| H(11B) | 0.050 | −0.416 | 0.660 | 0.074 |
| H(11C) | 0.205 | −0.313 | 0.650 | 0.074 |
| H(11D) | −0.261 | −0.409 | 0.950 | 0.050 |
| H(11E) | −0.114 | −0.313 | 0.961 | 0.050 |
| H(11F) | 0.070 | −0.478 | 1.037 | 0.054 |
| H(11G) | −0.062 | −0.576 | 1.018 | 0.054 |
| H(11H) | −0.200 | −0.437 | 1.160 | 0.061 |
| H(11I) | −0.322 | −0.543 | 1.145 | 0.061 |
| H(120) | −0.100 | −0.911 | 1.341 | 0.095 |
| H(121) | −0.247 | −0.763 | 1.222 | 0.076 |
| H(1N1) | 0.123 | −0.372 | 0.843 | 0.044 |
| H(1N2) | −0.003 | −0.469 | 0.838 | 0.044 |
| H(211) | 0.243 | −0.729 | 0.959 | 0.050 |
| H(217) | 0.364 | −0.328 | 0.465 | 0.062 |
| H(219) | 0.833 | −0.103 | 0.302 | 0.080 |
| H(21A) | 0.548 | −0.758 | 1.063 | 0.085 |
| H(21B) | 0.324 | −0.769 | 1.117 | 0.085 |
| H(21C) | 0.422 | −0.637 | 1.044 | 0.085 |
| H(21D) | 0.327 | −0.655 | 0.761 | 0.048 |
| H(21E) | 0.512 | −0.736 | 0.743 | 0.048 |
| H(21F) | 0.531 | −0.472 | 0.690 | 0.053 |
| H(21G) | 0.710 | −0.555 | 0.667 | 0.053 |
| H(21H) | 0.592 | −0.602 | 0.541 | 0.055 |
| H(21I) | 0.395 | −0.537 | 0.571 | 0.055 |
| H(220) | 1.030 | −0.270 | 0.364 | 0.080 |
| H(221) | 0.896 | −0.458 | 0.476 | 0.068 |
| H(2N1) | 0.487 | −0.581 | 0.865 | 0.048 |
| H(2N2) | 0.628 | −0.678 | 0.861 | 0.048 |

Hydrogens included in calculation of structure factors but not refined $U_{eq} = (1/3)S_iS_j U_{ij}a^*_i a^*_j a_i \cdot a_j$

TABLE 4

Anisotropic Temperature Factor Coefficients - U's for Cinacalcet HCl Form III

| Name | U(1, 1) | U(2, 2) | U(3, 3) | U(1, 2) | U(1, 3) | U(2, 3) |
|---|---|---|---|---|---|---|
| Cl(1) | 0.0332(11) | 0.0385(11) | 0.0707(14) | 0.0029(9) | −0.0181(9) | −0.0225(10) |
| Cl(2) | 0.0339(11) | 0.0349(11) | 0.0727(14) | −0.0004(8) | −0.0155(9) | −0.0187(10) |
| F(11) | 0.173(9) | 0.139(7) | 0.200(9) | −0.056(7) | −0.140(8) | 0.001(7) |
| F(12) | 0.109(7) | 0.268(13) | 0.311(15) | 0.096(8) | −0.134(9) | −0.168(12) |

TABLE 4-continued

Anisotropic Temperature Factor Coefficients - U's for Cinacalcet HCl Form III

| Name | U(1, 1) | U(2, 2) | U(3, 3) | U(1, 2) | U(1, 3) | U(2, 3) |
|---|---|---|---|---|---|---|
| F(13) | 0.125(7) | 0.293(13) | 0.096(6) | −0.072(8) | −0.030(5) | −0.069(7) |
| F(21) | 0.116(6) | 0.041(3) | 0.147(6) | −0.007(3) | −0.016(5) | 0.003(3) |
| F(22) | 0.095(5) | 0.076(4) | 0.097(4) | 0.028(4) | 0.012(4) | 0.009(3) |
| F(23) | 0.165(7) | 0.107(5) | 0.097(5) | 0.041(5) | −0.081(5) | −0.027(4) |
| N(112) | 0.037(4) | 0.033(3) | 0.046(3) | 0.003(3) | −0.011(3) | −0.017(3) |
| N(212) | 0.032(3) | 0.035(3) | 0.059(4) | 0.006(3) | −0.012(3) | −0.021(3) |
| C(11) | 0.039(5) | 0.041(5) | 0.044(5) | 0.000(4) | −0.008(4) | −0.012(4) |
| C(12) | 0.044(5) | 0.031(4) | 0.048(4) | −0.001(3) | −0.005(4) | −0.013(3) |
| C(13) | 0.059(6) | 0.045(5) | 0.049(5) | −0.004(4) | −0.011(4) | −0.015(4) |
| C(14) | 0.058(6) | 0.039(5) | 0.047(5) | 0.001(4) | −0.003(4) | −0.009(4) |
| C(15) | 0.045(5) | 0.044(5) | 0.046(4) | 0.005(4) | −0.002(4) | −0.015(4) |
| C(16) | 0.068(6) | 0.033(4) | 0.061(5) | 0.016(4) | −0.005(5) | −0.003(4) |
| C(17) | 0.056(6) | 0.059(6) | 0.070(6) | 0.015(5) | −0.020(5) | 0.000(5) |
| C(18) | 0.051(6) | 0.067(6) | 0.065(6) | 0.009(5) | −0.022(5) | −0.016(5) |
| C(19) | 0.040(5) | 0.053(5) | 0.057(5) | 0.006(4) | −0.015(4) | −0.017(4) |
| C(21) | 0.039(5) | 0.023(4) | 0.040(4) | 0.001(3) | −0.006(4) | −0.010(3) |
| C(22) | 0.050(5) | 0.034(4) | 0.046(4) | −0.004(4) | −0.010(4) | −0.011(3) |
| C(23) | 0.058(5) | 0.036(4) | 0.050(5) | 0.001(4) | −0.012(4) | −0.016(4) |
| C(24) | 0.046(5) | 0.037(4) | 0.047(5) | 0.003(4) | −0.008(4) | −0.014(4) |
| C(25) | 0.058(6) | 0.037(4) | 0.041(4) | −0.005(4) | −0.019(4) | −0.009(4) |
| C(26) | 0.057(6) | 0.043(5) | 0.050(5) | −0.014(5) | −0.008(4) | −0.013(4) |
| C(27) | 0.059(6) | 0.050(5) | 0.055(5) | −0.021(4) | −0.006(4) | −0.005(4) |
| C(28) | 0.044(5) | 0.050(5) | 0.054(5) | −0.007(4) | −0.003(4) | −0.010(4) |
| C(29) | 0.045(5) | 0.036(4) | 0.042(4) | −0.007(4) | −0.009(4) | −0.006(3) |
| C(38) | 0.075(8) | 0.052(6) | 0.074(7) | 0.001(5) | −0.014(6) | −0.005(5) |
| C(110) | 0.038(4) | 0.037(4) | 0.043(4) | 0.004(3) | −0.010(3) | −0.013(3) |
| C(111) | 0.043(5) | 0.041(5) | 0.038(4) | 0.002(4) | −0.012(3) | −0.015(3) |
| C(112) | 0.051(5) | 0.045(5) | 0.053(5) | −0.007(4) | −0.008(4) | −0.018(4) |
| C(113) | 0.043(5) | 0.043(5) | 0.041(4) | 0.004(4) | −0.010(4) | −0.017(4) |
| C(114) | 0.042(5) | 0.044(5) | 0.048(4) | −0.001(4) | −0.014(4) | −0.011(4) |
| C(115) | 0.040(5) | 0.052(5) | 0.050(5) | 0.002(4) | −0.007(4) | −0.004(4) |
| C(116) | 0.041(5) | 0.054(5) | 0.051(5) | −0.004(4) | −0.011(4) | −0.012(4) |
| C(117) | 0.056(5) | 0.046(5) | 0.050(5) | −0.001(4) | −0.012(4) | −0.009(4) |
| C(118) | 0.053(5) | 0.055(6) | 0.053(5) | 0.008(4) | −0.013(4) | −0.017(4) |
| C(119) | 0.109(9) | 0.060(7) | 0.054(6) | 0.026(6) | −0.033(6) | −0.010(5) |
| C(120) | 0.124(10) | 0.043(5) | 0.069(6) | −0.004(6) | −0.034(7) | −0.007(5) |
| C(121) | 0.087(8) | 0.052(6) | 0.056(6) | −0.023(5) | −0.027(5) | −0.016(4) |
| C(122) | 0.060(7) | 0.094(9) | 0.074(7) | −0.013(6) | −0.039(6) | 0.008(6) |
| C(210) | 0.031(4) | 0.026(3) | 0.037(4) | −0.007(3) | −0.004(3) | −0.002(3) |
| C(211) | 0.036(5) | 0.036(4) | 0.049(5) | −0.004(3) | −0.002(4) | −0.012(4) |
| C(212) | 0.073(6) | 0.045(5) | 0.052(5) | −0.005(4) | −0.006(4) | −0.021(4) |
| C(213) | 0.028(4) | 0.042(5) | 0.054(5) | 0.001(4) | −0.014(4) | −0.016(4) |
| C(214) | 0.045(5) | 0.045(5) | 0.042(4) | −0.001(4) | −0.007(4) | −0.014(3) |
| C(215) | 0.051(6) | 0.038(5) | 0.047(5) | 0.001(4) | −0.010(4) | −0.009(4) |
| C(216) | 0.058(6) | 0.039(4) | 0.041(4) | −0.003(4) | −0.010(4) | −0.012(4) |
| C(217) | 0.059(6) | 0.046(5) | 0.038(4) | −0.008(4) | 0.000(4) | −0.005(4) |
| C(219) | 0.078(8) | 0.070(6) | 0.043(5) | −0.022(5) | −0.007(5) | −0.007(4) |
| C(220) | 0.046(6) | 0.091(8) | 0.053(5) | −0.008(5) | −0.011(4) | −0.009(5) |
| C(221) | 0.058(6) | 0.059(6) | 0.049(5) | −0.002(5) | −0.013(4) | −0.011(4) |

The form of the anisotropic temperature factor is: $\exp[-2p\ h^2 a^{*2} U(1,1) + k^2 b^{*2} U(2,2) + l^2 c^{*2} U(3,3) + 2hka^*b^* U(1,2) + 2hla^*c^* U(1,3) + 2klb^*c^* U(2,3)]$ where $a^*$, $b^*$, and $c^*$ are reciprocal lattice constants.

TABLE 5

Table of Bond Distances in Angstroms for Cinacalcet HCl Form III

| Atom 1 | Atom 2 | Distance |
|---|---|---|
| F(11) | C(122) | 1.298(13) |
| F(12) | C(122) | 1.290(13) |
| F(13) | C(122) | 1.288(13) |
| F(21) | C(38) | 1.336(11) |
| F(22) | C(38) | 1.330(11) |
| F(23) | C(38) | 1.321(12) |
| N(112) | C(111) | 1.465(9) |
| N(112) | C(113) | 1.504(9) |
| N(212) | C(213) | 1.487(9) |
| N(212) | C(211) | 1.514(10) |
| C(11) | C(12) | 1.365(11) |
| C(11) | C(110) | 1.445(10) |
| C(11) | C(111) | 1.509(11) |
| C(12) | C(13) | 1.403(10) |
| C(13) | C(14) | 1.354(11) |
| C(14) | C(15) | 1.434(12) |
| C(15) | C(110) | 1.421(11) |
| C(15) | C(16) | 1.421(11) |
| C(16) | C(17) | 1.349(13) |
| C(17) | C(18) | 1.365(13) |
| C(18) | C(19) | 1.386(11) |
| C(19) | C(110) | 1.396(11) |
| C(21) | C(22) | 1.380(11) |
| C(21) | C(210) | 1.421(10) |
| C(21) | C(211) | 1.519(10) |
| C(22) | C(23) | 1.412(10) |
| C(23) | C(24) | 1.330(11) |
| C(24) | C(25) | 1.428(11) |
| C(25) | C(26) | 1.397(11) |
| C(25) | C(210) | 1.434(10) |

TABLE 5-continued

Table of Bond Distances in Angstroms for Cinacalcet HCl Form III

| Atom 1 | Atom 2 | Distance |
|---|---|---|
| C(26) | C(27) | 1.367(12) |
| C(27) | C(28) | 1.384(12) |
| C(28) | C(29) | 1.374(11) |
| C(29) | C(210) | 1.424(10) |
| C(38) | C(218) | 1.489(12) |
| C(111) | C(112) | 1.522(11) |
| C(113) | C(114) | 1.518(10) |
| C(114) | C(115) | 1.522(11) |
| C(115) | C(116) | 1.499(11) |
| C(116) | C(121) | 1.380(12) |
| C(116) | C(117) | 1.399(11) |
| C(117) | C(118) | 1.390(11) |
| C(118) | C(119) | 1.364(13) |
| C(118) | C(122) | 1.470(13) |
| C(119) | C(120) | 1.349(15) |
| C(120) | C(121) | 1.408(13) |
| C(211) | C(212) | 1.494(11) |
| C(213) | C(214) | 1.514(11) |
| C(214) | C(215) | 1.492(11) |
| C(215) | C(216) | 1.488(11) |
| C(216) | C(217) | 1.401(11) |
| C(216) | C(221) | 1.401(12) |
| C(217) | C(218) | 1.378(12) |
| C(218) | C(219) | 1.389(13) |
| C(219) | C(220) | 1.406(13) |
| C(220) | C(221) | 1.361(12) |

Numbers in parentheses are estimated standard deviations in the least significant digits.

TABLE 6

Table of Bond Angles in Degrees for Cinacalcet HCl Form III

| Atom 1 | Atom 2 | Atom 3 | Angle |
|---|---|---|---|
| C(111) | N(112) | C(113) | 116.0(5) |
| C(213) | N(212) | C(211) | 117.0(6) |
| C(12) | C(11) | C(110) | 119.6(7) |
| C(12) | C(11) | C(111) | 121.2(7) |
| C(110) | C(11) | C(111) | 119.1(7) |
| C(11) | C(12) | C(13) | 121.6(7) |
| C(14) | C(13) | C(12) | 121.2(8) |
| C(13) | C(14) | C(15) | 119.4(8) |
| C(110) | C(15) | C(16) | 118.9(8) |
| C(110) | C(15) | C(14) | 120.3(7) |
| C(16) | C(15) | C(14) | 120.8(8) |
| C(17) | C(16) | C(15) | 120.6(8) |
| C(16) | C(17) | C(18) | 120.7(8) |
| C(17) | C(18) | C(19) | 121.2(9) |
| C(18) | C(19) | C(110) | 120.2(8) |
| C(22) | C(21) | C(210) | 118.8(6) |
| C(22) | C(21) | C(211) | 120.9(7) |
| C(210) | C(21) | C(211) | 120.1(6) |
| C(21) | C(22) | C(23) | 121.5(8) |
| C(24) | C(23) | C(22) | 120.3(8) |
| C(23) | C(24) | C(25) | 121.9(7) |
| C(26) | C(25) | C(24) | 122.6(7) |
| C(26) | C(25) | C(210) | 119.5(8) |
| C(24) | C(25) | C(210) | 117.8(7) |
| C(27) | C(26) | C(25) | 121.0(8) |
| C(26) | C(27) | C(28) | 120.8(8) |
| C(29) | C(28) | C(27) | 120.2(8) |
| C(28) | C(29) | C(210) | 121.3(7) |
| F(23) | C(38) | F(22) | 106.1(9) |
| F(23) | C(38) | F(21) | 104.6(8) |
| F(22) | C(38) | F(21) | 105.8(9) |
| F(23) | C(38) | C(218) | 112.6(8) |
| F(22) | C(38) | C(218) | 112.9(8) |
| F(21) | C(38) | C(218) | 114.1(8) |
| C(19) | C(110) | C(15) | 118.4(6) |
| C(19) | C(110) | C(11) | 123.7(7) |
| C(15) | C(110) | C(11) | 117.9(7) |
| N(112) | C(111) | C(11) | 114.5(6) |

TABLE 6-continued

Table of Bond Angles in Degrees for Cinacalcet HCl Form III

| Atom 1 | Atom 2 | Atom 3 | Angle |
|---|---|---|---|
| N(112) | C(111) | C(112) | 107.2(6) |
| C(11) | C(111) | C(112) | 109.6(7) |
| N(112) | C(113) | C(114) | 109.0(6) |
| C(113) | C(114) | C(115) | 113.2(6) |
| C(116) | C(115) | C(114) | 109.9(7) |
| C(121) | C(116) | C(117) | 117.9(8) |
| C(121) | C(116) | C(115) | 121.8(8) |
| C(117) | C(116) | C(115) | 120.0(8) |
| C(118) | C(117) | C(116) | 119.9(8) |
| C(119) | C(118) | C(117) | 121.7(9) |
| C(119) | C(118) | C(122) | 119.5(8) |
| C(117) | C(118) | C(122) | 118.7(9) |
| C(120) | C(119) | C(118) | 118.9(8) |
| C(119) | C(120) | C(121) | 121.2(9) |
| C(116) | C(121) | C(120) | 120.4(9) |
| F(13) | C(122) | F(12) | 104.9(10) |
| F(13) | C(122) | F(11) | 102.6(12) |
| F(12) | C(122) | F(11) | 101.8(11) |
| F(13) | C(122) | C(118) | 113.8(10) |
| F(12) | C(122) | C(118) | 115.6(11) |
| F(11) | C(122) | C(118) | 116.5(8) |
| C(21) | C(210) | C(29) | 123.2(6) |
| C(21) | C(210) | C(25) | 119.6(7) |
| C(29) | C(210) | C(25) | 117.2(7) |
| C(212) | C(211) | N(212) | 109.0(7) |
| C(212) | C(211) | C(21) | 113.7(7) |
| N(212) | C(211) | C(21) | 110.9(6) |
| N(212) | C(213) | C(214) | 109.4(6) |
| C(215) | C(214) | C(213) | 114.1(7) |
| C(216) | C(215) | C(214) | 112.6(7) |
| C(217) | C(216) | C(221) | 118.0(8) |
| C(217) | C(216) | C(215) | 122.0(8) |
| C(221) | C(216) | C(215) | 119.9(7) |
| C(218) | C(217) | C(216) | 119.8(9) |
| C(217) | C(218) | C(219) | 122.2(8) |
| C(217) | C(218) | C(38) | 118.6(9) |
| C(219) | C(218) | C(38) | 119.1(8) |
| C(218) | C(219) | C(220) | 117.7(9) |
| C(221) | C(220) | C(219) | 120.4(9) |
| C(220) | C(221) | C(216) | 121.9(8) |

Numbers in parentheses are estimated standard deviations in the least significant digits.

TABLE 7

Table of Torsion Angles in Degrees for Cinacalcet HCl Form III

| Atom 1 | Atom 2 | Atom 3 | Atom 4 | Angle |
|---|---|---|---|---|
| C(113) | N(112) | C(111) | C(11) | 66.94 (0.88) |
| C(113) | N(112) | C(111) | C(112) | 171.29 (0.64) |
| C(111) | N(112) | C(113) | C(114) | 174.98 (0.65) |
| C(213) | N(212) | C(211) | C(21) | 60.11 (0.88) |
| C(213) | N(212) | C(211) | C(212) | −173.99 (0.69) |
| C(211) | N(212) | C(213) | C(214) | 167.97 (0.65) |
| C(110) | C(11) | C(12) | C(13) | 0.02 (1.28) |
| C(111) | C(11) | C(12) | C(13) | 176.98 (0.73) |
| C(12) | C(11) | C(110) | C(15) | 1.23 (1.13) |
| C(12) | C(11) | C(110) | C(19) | −179.73 (0.76) |
| C(111) | C(11) | C(110) | C(15) | −175.79 (0.70) |
| C(111) | C(11) | C(110) | C(19) | 3.25 (1.17) |
| C(12) | C(11) | C(111) | N(112) | 31.40 (1.07) |
| C(12) | C(11) | C(111) | C(112) | −89.06 (0.90) |
| C(110) | C(11) | C(111) | N(112) | −151.63 (0.70) |
| C(110) | C(11) | C(111) | C(112) | 87.91 (0.90) |
| C(11) | C(12) | C(13) | C(14) | −0.79 (1.24) |
| C(12) | C(13) | C(14) | C(15) | 0.24 (1.21) |
| C(13) | C(14) | C(15) | C(16) | 178.68 (0.79) |
| C(13) | C(14) | C(15) | C(110) | 1.06 (1.18) |
| C(14) | C(15) | C(16) | C(17) | −178.95 (0.83) |
| C(110) | C(15) | C(16) | C(17) | −1.29 (1.27) |
| C(14) | C(15) | C(110) | C(11) | −1.77 (1.12) |
| C(14) | C(15) | C(110) | C(19) | 179.14 (0.73) |
| C(16) | C(15) | C(110) | C(11) | −179.44 (0.75) |

TABLE 7-continued

Table of Torsion Angles in Degrees for Cinacalcet HCl Form III

| Atom 1 | Atom 2 | Atom 3 | Atom 4 | Angle |
|---|---|---|---|---|
| C(16) | C(15) | C(110) | C(19) | 1.47 (1.13) |
| C(15) | C(16) | C(17) | C(18) | 0.72 (1.40) |
| C(16) | C(17) | C(18) | C(19) | −0.34 (1.42) |
| C(17) | C(18) | C(19) | C(110) | 0.55 (1.30) |
| C(18) | C(19) | C(110) | C(11) | 179.85 (0.79) |
| C(18) | C(19) | C(110) | C(15) | −1.12 (1.16) |
| C(210) | C(21) | C(22) | C(23) | −0.49 (1.15) |
| C(211) | C(21) | C(22) | C(23) | 174.50 (0.72) |
| C(22) | C(21) | C(210) | C(25) | 1.31 (1.06) |
| C(22) | C(21) | C(210) | C(29) | −179.20 (0.71) |
| C(211) | C(21) | C(210) | C(25) | −173.72 (0.67) |
| C(211) | C(21) | C(210) | C(29) | 5.77 (1.09) |
| C(22) | C(21) | C(211) | N(212) | 39.51 (1.00) |
| C(22) | C(21) | C(211) | C(212) | −83.71 (0.95) |
| C(210) | C(21) | C(211) | N(212) | −145.57 (0.69) |
| C(210) | C(21) | C(211) | C(212) | 91.21 (0.93) |
| C(21) | C(22) | C(23) | C(24) | 0.67 (1.22) |
| C(22) | C(23) | C(24) | C(25) | −1.69 (1.22) |
| C(23) | C(24) | C(25) | C(26) | 179.07 (0.79) |
| C(23) | C(24) | C(25) | C(210) | 2.46 (1.16) |
| C(24) | C(25) | C(26) | C(27) | −177.75 (0.79) |
| C(210) | C(25) | C(26) | C(27) | −1.19 (1.19) |
| C(24) | C(25) | C(210) | C(21) | −2.23 (1.04) |
| C(24) | C(25) | C(210) | C(29) | 178.24 (0.68) |
| C(26) | C(25) | C(210) | C(21) | −178.95 (0.70) |
| C(26) | C(25) | C(210) | C(29) | 1.52 (1.04) |
| C(25) | C(26) | C(27) | C(28) | 0.70 (1.31) |
| C(26) | C(27) | C(28) | C(29) | −0.58 (1.29) |
| C(27) | C(28) | C(29) | C(210) | 0.98 (1.24) |
| C(28) | C(29) | C(210) | C(21) | 179.06 (0.72) |
| C(28) | C(29) | C(210) | C(25) | −1.44 (1.07) |
| F(21) | C(38) | C(218) | C(217) | 160.65 (0.83) |
| F(21) | C(38) | C(218) | C(219) | −22.83 (1.26) |
| F(22) | C(38) | C(218) | C(217) | 39.86 (1.23) |
| F(22) | C(38) | C(218) | C(219) | −143.63 (0.90) |
| F(23) | C(38) | C(218) | C(217) | −80.32 (1.10) |
| F(23) | C(38) | C(218) | C(219) | 96.20 (1.12) |
| N(112) | C(113) | C(114) | C(115) | −174.90 (0.67) |
| C(113) | C(114) | C(115) | C(116) | −175.54 (0.73) |
| C(114) | C(115) | C(116) | C(117) | 85.82 (0.97) |
| C(114) | C(115) | C(116) | C(121) | −87.67 (1.03) |
| C(115) | C(116) | C(117) | C(118) | −174.81 (0.76) |
| C(121) | C(116) | C(117) | C(118) | −1.07 (1.23) |
| C(115) | C(116) | C(121) | C(120) | 174.77 (0.89) |
| C(117) | C(116) | C(121) | C(120) | 1.14 (1.37) |
| C(116) | C(117) | C(118) | C(119) | 0.74 (1.30) |
| C(116) | C(117) | C(118) | C(122) | −177.17 (0.84) |
| C(117) | C(118) | C(119) | C(120) | −0.45 (1.45) |
| C(122) | C(118) | C(119) | C(120) | 177.45 (0.98) |
| C(117) | C(118) | C(122) | F(11) | −12.49 (1.47) |
| C(117) | C(118) | C(122) | F(12) | −131.95 (1.16) |
| C(117) | C(118) | C(122) | F(13) | 106.56 (1.24) |
| C(119) | C(118) | C(122) | F(11) | 169.55 (1.04) |
| C(119) | C(118) | C(122) | F(12) | 50.10 (1.46) |
| C(119) | C(118) | C(122) | F(13) | −71.40 (1.47) |
| C(118) | C(119) | C(120) | C(121) | 0.52 (1.59) |
| C(119) | C(120) | C(121) | C(116) | −0.89 (1.60) |
| N(212) | C(213) | C(214) | C(215) | −176.37 (0.68) |
| C(213) | C(214) | C(215) | C(216) | 171.63 (0.72) |
| C(214) | C(215) | C(216) | C(217) | −108.21 (0.94) |
| C(214) | C(215) | C(216) | C(221) | 68.22 (1.02) |
| C(215) | C(216) | C(217) | C(218) | 173.28 (0.76) |
| C(221) | C(216) | C(217) | C(218) | −3.21 (1.21) |
| C(215) | C(216) | C(221) | C(220) | −174.91 (0.84) |
| C(217) | C(216) | C(221) | C(220) | 1.66 (1.32) |
| C(216) | C(217) | C(218) | C(38) | 179.40 (0.79) |
| C(216) | C(217) | C(218) | C(219) | 2.99 (1.30) |
| C(38) | C(218) | C(219) | C(220) | −177.44 (0.87) |
| C(217) | C(218) | C(219) | C(220) | −1.06 (1.35) |
| C(218) | C(219) | C(220) | C(221) | −0.57 (1.42) |
| C(219) | C(220) | C(221) | C(216) | 0.24 (1.46) |

All of the compositions and/or methods disclosed and claimed herein can be made and executed without undue experimentation in light of the present disclosure. While the compositions and methods of this invention have been described in terms of specific embodiments, it will be apparent to those of skill in the art that variations of the compositions and/or methods and in the steps or in the sequence of steps of the method described herein can be made without departing from the concept, spirit and scope of the invention. More specifically, it will be apparent that certain agents which are both chemically and physiologically related may be substituted for the agents described herein while the same or similar results are achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

The invention claimed is:

1. A method of preparing a crystalline polymorph of N-[1-(R)-(−)-(1-naphthyl)ethyl]-3-[-3-(trifluoromethyl)phenyl]-1-aminopropane hydrochloride having a powder X ray powder diffraction (XRPD) pattern having peaks at diffraction angle 2 θ of 16.6942; 17.6152; 19.4992; 20.2946; and 20.5877, said method comprising:
   a. melting cinacalcet polymorph Form I at 190° C. and quenching said amorphous form in a cooling bath of dry ice and acetone for 30 minutes;
   b. grinding said quenched amorphous form to reduce particle size of said quenched amorphous form, and
   c. heating the amorphous quenched, size-reduced particles from step (b) at 90° C. for approximately 3.5 hours.

2. The method of claim 1, wherein said size-reduced particles have a particle size of about 38 μm.

3. The method of claim 1, wherein said size-reduced particles have a particle size of about 125 μm.

4. The method of claim 1 wherein the XRPD pattern further comprises at least one diffraction angle 2 θ peak selected from the group consisting of 12.3402; 14.4334; 15.3545; 16.443; 18.2013; 18.6618; 19.9178; 21.7599; 21.9692; 22.4297; 24.0206; and 25.0672.

5. The method of claim 1 wherein the crystalline polymorph has an XRPD pattern that comprises at least diffraction angle 2 θ peaks at 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672.

6. The method of claim 1 wherein the XRPD pattern comprises diffraction angle 2 θ peaks at 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672.

7. The method of claim 1 wherein said polymorph comprises an XRPD pattern substantially as shown in FIG. 1, 2 or 3.

8. The method of claim 1 wherein the crystalline polymorph has positional parameters substantially as shown in Table 3.

9. The method of claim 1 wherein the crystalline polymorph has an anisotropic temperature factor coefficient substantially as shown in Table 4.

10. The method of claim 1 wherein the crystalline polymorph has bond distance characteristics substantially as shown in Table 5.

11. The method of claim 1 wherein the crystalline polymorph has bond angle characteristics substantially as shown in Table 6.

12. The method of claim 1 wherein the crystalline polymorph has torsion angle characteristics substantially as shown in Table 7.

13. A crystalline polymorph of N-[1-(R)-(−)-(1-naphthyl)ethyl]-3-[3-(trifluoromethyl)phenyl]-1-aminopropane hydrochloride having a powder X ray powder diffraction (XRPD) pattern having peaks at diffraction angle 2 Θ of about 16.6942; 17.6152; 19.4992; 20.2946; and 20.5877.

14. The crystalline polymorph of claim 13 wherein the XRPD pattern further comprises at least one diffraction angle 2 Θ peak selected from the group consisting of 12.3402; 14.4334; 15.3545; 16.443; 18.2013; 18.6618; 19.9178; 21.7599; 21.9692; 22.4297; 24.0206;and 25.0672.

15. The crystalline polymorph of claim 13 having an XRPD pattern that comprises at least diffraction angle 2 Θ peaks at about 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672.

16. The crystalline polymorph of claim 13 wherein the XRPD pattern comprises diffraction angle 2 Θ peaks at about 12.3402; 14.4334; 15.3545; 16.443; 16.6942; 17.6152; 18.2013; 18.6618; 19.4992; 19.9178; 20.2946; 20.5877; 21.7599; 21.9692; 22.4297; 24.0206; and 25.0672.

17. The crystalline polymorph of claim 13 wherein said polymorph comprises an XRPD pattern substantially as shown in FIG. 1, 2 or 3.

18. The crystalline polymorph of claim 13 having positional parameters substantially as shown in Table 3.

19. The crystalline polymorph of claim 13 having an anisotropic temperature factor coefficient substantially as shown in Table 4.

20. The crystalline polymorph of claim 13 having bond distance characteristics substantially as shown in Table 5.

21. The crystalline polymorph of claim 13 having bond angle characteristics substantially as shown in Table 6.

22. The crystalline polymorph of claim 13 having torsion angle characteristics substantially as shown in Table 7.

23. A pharmaceutical composition comprising a polymorph of claim 13 and at least one pharmaceutically acceptable carrier.

* * * * *